(12) United States Patent
Berthelette et al.

(10) Patent No.: US 9,023,864 B2
(45) Date of Patent: May 5, 2015

(54) INDOLE DERIVATIVES AS CRTH2 RECEPTOR ANTAGONISTS

(71) Applicants: Carl Berthelette, Ste-Dorothee (CA); Michael Boyd, Winchester, MA (US); John Colucci, Kirkland (CA); Karine Villeneuve, Montreal (CA); Joey L. Methot, Westwood, MA (US)

(72) Inventors: Carl Berthelette, Ste-Dorothee (CA); Michael Boyd, Winchester, MA (US); John Colucci, Kirkland (CA); Karine Villeneuve, Montreal (CA); Joey L. Methot, Westwood, MA (US)

(73) Assignees: Merck Sharp & Dohme Corp., Rahway, NJ (US); Merck Canada Inc., Quebec (CA)

( * ) Notice: Subject to any disclaimer, the term of this patent is extended or adjusted under 35 U.S.C. 154(b) by 16 days.

(21) Appl. No.: 13/762,050

(22) Filed: Feb. 7, 2013

(65) Prior Publication Data

US 2013/0150398 A1    Jun. 13, 2013

Related U.S. Application Data

(63) Continuation of application No. 12/708,924, filed on Feb. 19, 2010, now Pat. No. 8,394,819.

(60) Provisional application No. 61/154,968, filed on Feb. 24, 2009.

(51) Int. Cl.
| | | |
|---|---|---|
| *A61K 31/404* | (2006.01) |
| *A61K 31/4353* | (2006.01) |
| *C07D 451/02* | (2006.01) |
| *C07D 487/04* | (2006.01) |
| *C07D 471/04* | (2006.01) |
| *C07D 403/04* | (2006.01) |
| *C07D 403/08* | (2006.01) |

(52) U.S. Cl.
CPC ............ *C07D 471/04* (2013.01); *C07D 403/04* (2013.01); *C07D 403/08* (2013.01)

(58) Field of Classification Search
CPC ... C07D 471/04; C07D 403/04; C07D 403/08
USPC ................ 514/44, 294, 411; 546/94; 548/255
See application file for complete search history.

(56) References Cited

U.S. PATENT DOCUMENTS

| | | |
|---|---|---|
| 7,696,222 B2 | 4/2010 | Wang |
| 2011/0172263 A1 | 7/2011 | Colucci et al. |
| 2011/0178115 A1 | 7/2011 | Leblanc et al. |
| 2011/0201641 A1 | 8/2011 | Wang |

FOREIGN PATENT DOCUMENTS

| | | |
|---|---|---|
| WO | 2003/097598 A1 | 11/2003 |
| WO | 2006/015191 A2 | 2/2006 |
| WO | 2007/019675 A1 | 2/2007 |
| WO | 2008/017989 A1 | 2/2008 |
| WO | 2009/140642 A2 | 11/2009 |
| WO | 2010/031182 A1 | 3/2010 |
| WO | 2010/031183 A1 | 3/2010 |
| WO | 2010/085820 A2 | 7/2010 |

OTHER PUBLICATIONS

Ulven, et al., "Minor Structural Modifications Convert the Dual TP/CRTH2 Antagonist Ramatroban into a Highly Selective and Potent CRTH2 Antagonist," American Chemical Society, 2005, vol. 48, No. 4, pp. 897-900.

*Primary Examiner* — Shawquia Jackson
(74) *Attorney, Agent, or Firm* — Eric A. Meade; Catherine D. Fitch

(57) ABSTRACT

Compound of formula I are antagonists of the PGD2 receptor, CRTH2, and as such are useful in the treatment and/or prevention of CRTH2-mediated diseases such as asthma.

10 Claims, 4 Drawing Sheets

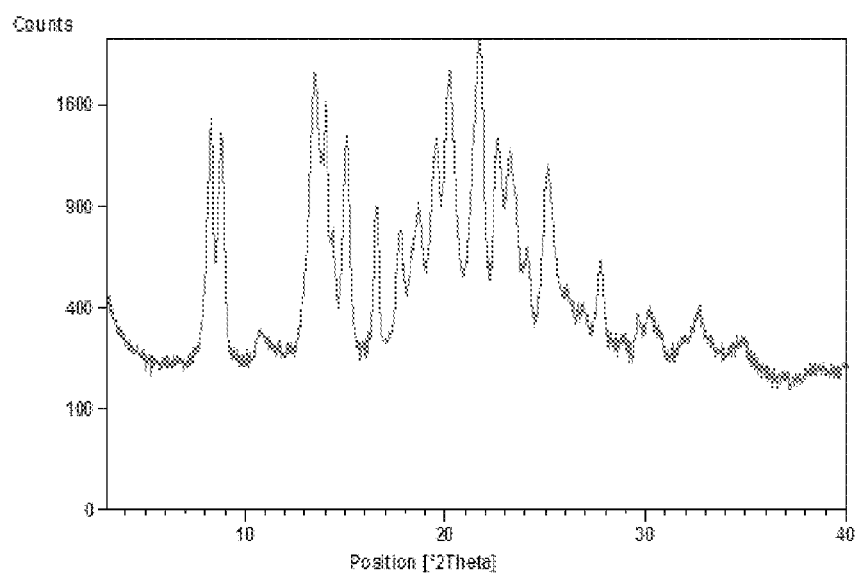
FIGURE 1. X-ray powder diffraction pattern for crystalline Form B of compound of Example 8A.

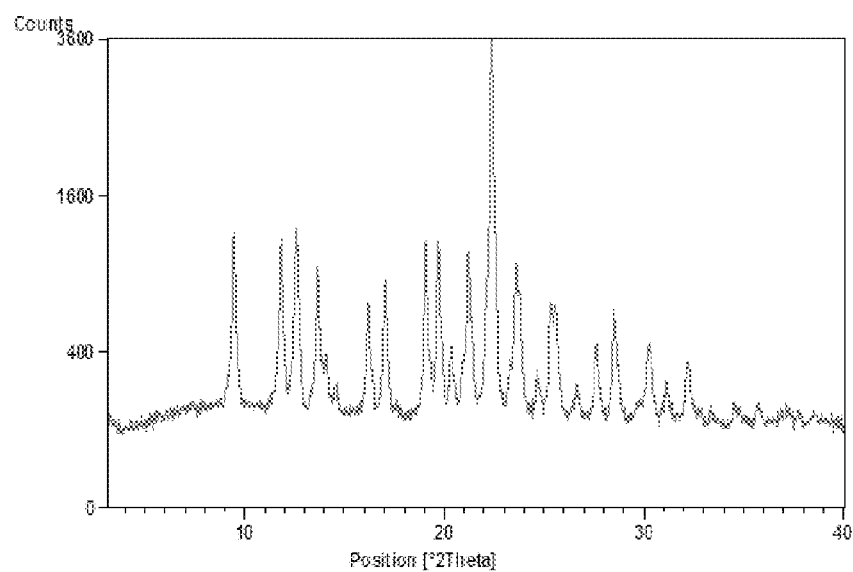
FIGURE 2. X-ray powder diffraction pattern for crystalline Form C of compound of Example 8A.

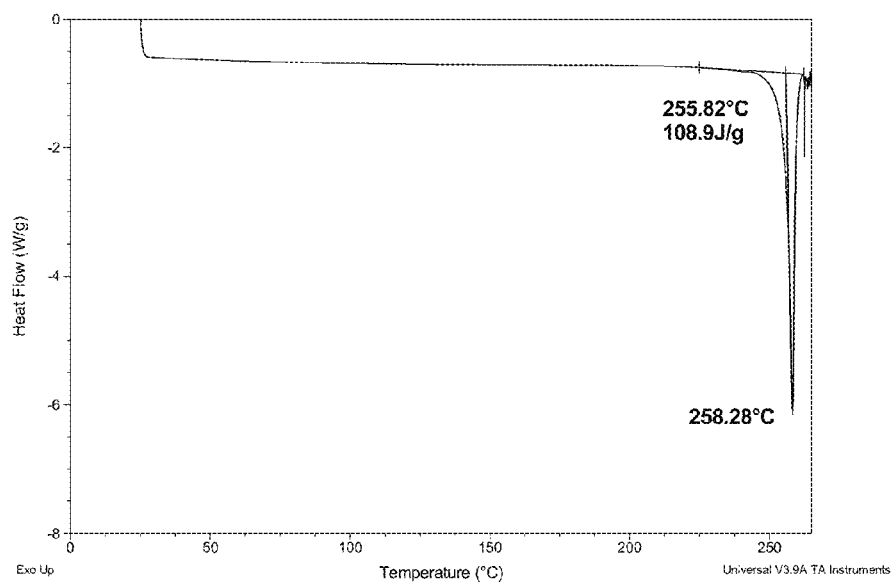
FIGURE 3. DSC curve for crystalline Form B of compound of Example 8A.

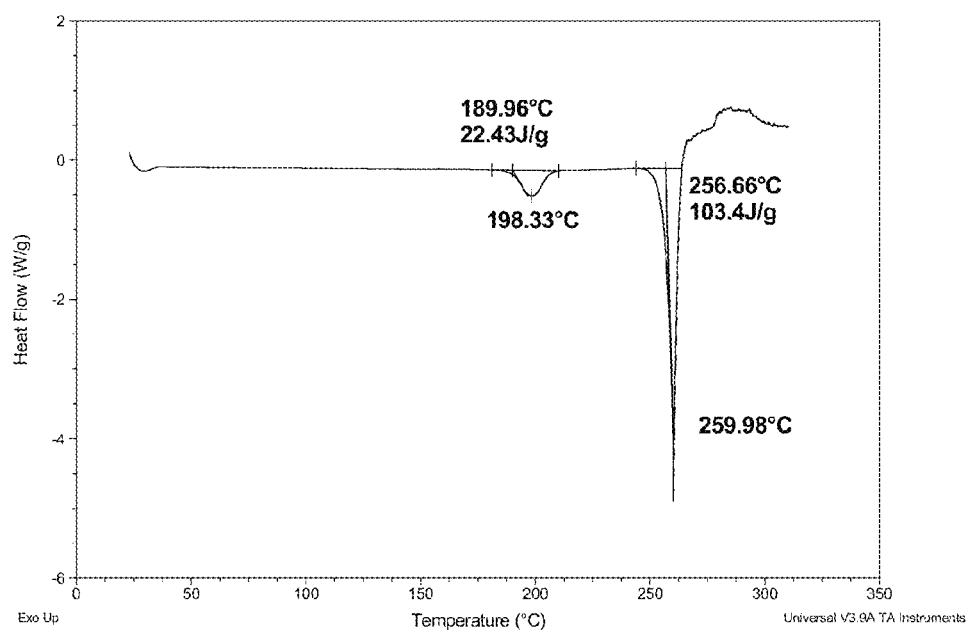
FIGURE 4. DSC curve for crystalline Form C of compound of Example 8A.

INDOLE DERIVATIVES AS CRTH2 RECEPTOR ANTAGONISTS

CROSS REFERENCE TO RELATED APPLICATIONS

This application is a continuation of U.S. application Ser. No. 12/708,924, filed Feb. 19, 2010, which claims priority under 35 U.S.C. §119(e) from U.S. Provisional Application No. 61/154,968, filed Feb. 24, 2009.

BACKGROUND OF THE INVENTION

Prostanglandin $D_2$ ($PGD_2$) is a cyclooxygenase metabolite of arachidonic acid. It is released from mast and TH2 cells in response to an immunological challenge, and has been implicated in playing a role in different physiological events such as sleep and allergic responses.

Receptors for $PGD_2$ include the "DP" receptor, the chemoattractant receptor-homologous molecule expressed on TH2 cells ("CRTH2"), and the "FP" receptor. These receptors are G-protein coupled receptors activated by $PGD_2$. The CRTH2 receptor and its expression on different cells including human T-helper cells, basophils, and eosinophils are described in Abe, et al., *Gene* 227:71-77, 1999, Nagata, et al., *FEBS Letters* 459:195-199, 1999, and Nagata, et al., *The Journal of Immunology* 162:1278-1286, 1999, describe CRTH2 receptor. Hirai, et al., *J. Exp. Med.* 193:255-261, 2001, indicates that CRTH2 is a receptor for $PGD_2$.

WO2007019675 discloses CRTH2 antagonists of the formula:

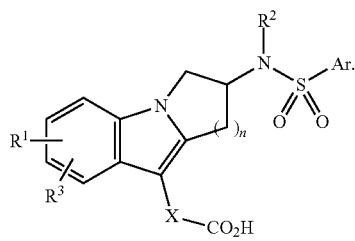

SUMMARY OF THE INVENTION

The present invention provides novel compounds which are CRTH2 receptor antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

BRIEF DESCRIPTION OF THE DRAWINGS

FIG. 1 depicts an X-ray powder diffraction pattern for crystalline Form B of compound of Example 8A.

FIG. 2 depicts an X-ray powder diffraction pattern for crystalline Form C of compound of Example 8A.

FIG. 3 depicts a differential scanning calorimetry (DSC) curve for crystalline Form B of compound of Example 8A.

FIG. 4 depicts a differential scanning calorimetry (DSC) curve for crystalline Form C of compound of Example 8A.

DETAILED DESCRIPTION OF THE INVENTION

The present invention relates to compounds of formula I:

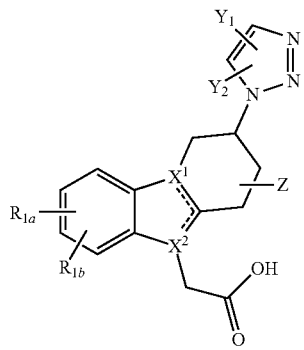

and pharmaceutically acceptable salts thereof, wherein:

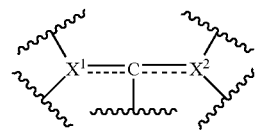

represents either

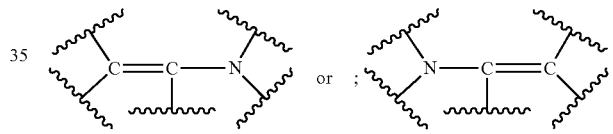

$Y_1$ is selected from optionally substituted aryl and —$C(R_2)(R_3)(R_4)$;

$Y_2$ is selected from H and —$C_{1-6}$(alkyl);

Z is selected from H and —$C_{1-6}$(alkyl);

$R_{1a}$ and $R_{1b}$ are independently selected from H, halogen, —$OC_{1-6}$alkyl, —O-halo$C_{1-6}$alkyl, —$C_{1-6}$alkyl, halo$C_{1-6}$alkyl, optionally substituted aryl and —($C_{1-3}$alkylene)-optionally substituted aryl;

$R_2$ is selected from H, —$C_{1-6}$alkyl optionally substituted with halogen, —OH or —$NHSO_2CH_3$, —OH, —$OC_{1-6}$alkyl, —$S(O)_nC_{1-6}$alkyl, —CN, optionally substituted aryl, optionally substituted —O-aryl and optionally substituted heteroaryl, wherein n is 0, 1 or 2;

$R_3$ is selected from H, —$C_{1-6}$alkyl, $C_{1-6}$haloalkyl, optionally substituted aryl and optionally substituted heteroaryl; and $R_4$ is selected from H, —$C_{1-6}$alkyl, $C_{1-6}$haloalkyl, optionally substituted aryl and optionally substituted heteroaryl; or $R_3$, $R_4$ and the carbon atom to which they are attached together form —$C_{3-6}$cycloalkyl, fluorenyl or —$C_{3-6}$heterocyclyl having a ring heteroatom selected from —$N(R^a)$—, —O— and —S—; or $R_3$, $R_4$ together represent $C_{1-6}$alkylidene;

$R^a$ is H, $C_{1-6}$alkyl or —$C(O)C_{1-6}$alkyl; and the optional substituent for aryl and heteroaryl is 1 to 4 groups independently selected from halogen, —$C_{1-3}$alkoxy, —$C_{1-3}$halo alkyl, hydroxy-$C_{1-3}$ alkyl, —S(O)n-$C_{1-3}$ alkyl, amino, and mono- and di-($C_{1-3}$alkyl)amino.

In one subset of formula I are compounds wherein $R_{1b}$, $Y_2$ and Z are each H.

In one subset of formula I are compounds of formula Ia and pharmaceutically acceptable salts thereof:

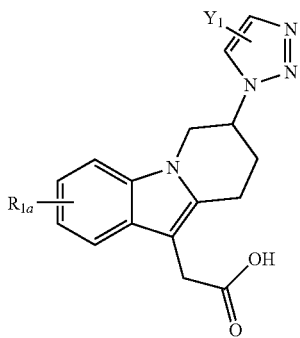

In another subset of formula I are compounds of formula Ib and pharmaceutically acceptable salts thereof:

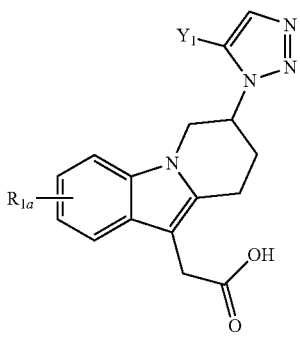

In another subset of formula I are compounds of formula Ic and pharmaceutically acceptable salts thereof:

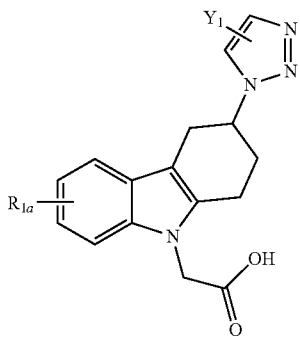

In one group within formulas I, Ia, Ib and Ic are compounds wherein $R_{1a}$ is H or halogen. In one embodiment, $R_{1a}$ is H. In another embodiment $R_{1a}$ is F.

In another group within formulas I, Ia, Ib and Ic are compounds wherein $Y_1$ is optionally substituted aryl. In one embodiment $Y_1$ is phenyl optionally substituted with 1 to 3 groups independently selected from halogen, —$C_{1-3}$alkoxy, —$C_{1-3}$haloalkyl, hydroxy-$C_{1-3}$alkyl, —S(O)n-$C_{1-3}$alkyl, amino, and mono- and di-($C_{1-3}$alkyl)amino.

In another group within formulas I, Ia, Ib and Ic are compounds wherein $Y_1$ is —C($R_3$)($R_4$)-optionally substituted phenyl or —CH$_2$O-optionally substituted phenyl. In one embodiment $R_3$ and $R_4$ are each H. In a second embodiment one of $R_3$ and $R_4$ is OH and the other is H, $C_{1-3}$alkyl or optionally substituted phenyl. In a third embodiment $R_3$, $R_4$ and the carbon atom to which they are attached together form —$C_{3-6}$cycloalkyl. In a fourth embodiment one of $R_3$ and $R_4$ is H and the other is $C_{1-3}$alkyl or optionally substituted phenyl. In a fifth embodiment, $R_3$ and $R_4$ together represent —$C_{1-3}$ alkylidene. Within this group optional substituents for phenyl are 1 to 3 groups independently selected from halogen, —$C_{1-3}$ alkoxy, —$C_{1-3}$haloalkyl, hydroxy-$C_{1-3}$ alkyl, —S(O)n-$C_{1-3}$ alkyl, amino, and mono- and di-($C_{1-3}$alkyl)amino; more particularly the optional substituent is 1 or 2 halogen atoms.

In another group within formulas Ia and Ib are compounds wherein $R_{1a}$ is H or F, and $Y_1$ is selected from optionally substituted phenyl, —C($R_3$)($R_4$)-optionally substituted phenyl and —CH$_2$O-optionally substituted phenyl. Within this group are compounds of formula Ib wherein $Y_1$ is —C($R_3$)($R_4$)-optionally substituted phenyl, and (i) one of $R_3$ and $R_4$ is H or OH, and the other is H, —$C_{1-3}$alkyl or optionally substituted phenyl; or (ii) $R_3$, $R_4$ and the carbon atom to which they are attached together form —$C_{3-6}$cycloalkyl; or (iii) $R_3$ and $R_4$ together together represent —$C_{1-3}$alkylidene.

In another group within formulas Ib are compounds wherein $R_{1a}$ is H or F, and $Y_1$ is —CH$_2$-phenyl optionally substituted with 1 or 2 groups independently selected from halogen, —$C_{1-3}$alkoxy, —$C_{1-3}$halo alkyl, hydroxy-$C_{1-3}$ alkyl, —S(O)n-$C_{1-3}$ alkyl, amino, and mono- and di-($C_{1-3}$alkyl) amino; more particularly the optional substituent is 1 or 2 halogen atoms.

Representative compounds of the present invention (including pharmaceutically acceptable salts thereof) are:

[7-(4-benzyl-[1,2,3]triazol-1-yl)-6,7,8,9-tetrahydropyrido[1,2-α]indol-10-yl]-acetic acid;

{7-[4-(4-methoxy-phenyl)-[1,2,3]triazol-1-yl]-6,7,8,9-tetrahydropyrido[1,2-α]indol-10-yl}-acetic acid;

[7-(5-benzyl-[1,2,3]triazol-1-yl)-6,7,8,9-tetrahydropyrido[1,2-α]indol-10-yl]-acetic acid;

(7-{5-[(2,6-dichlorophenoxy)methyl]-1H-1,2,3-triazol-1-yl}-6,7,8,9-tetrahydropyrido[1,2-α]indol-10-yl)acetic acid;

(7-{5-[1-(4-fluoro-phenyl)-1-hydroxy-ethyl]-[1,2,3]triazol-1-yl}-6,7,8,9-tetrahydropyrido[1,2-α]indol-10-yl)-acetic acid;

{7-[5-(1-phenyl-cyclopentyl)-[1,2,3]triazol-1-yl]-6,7,8,9-tetrahydropyrido[1,2-α]indol-10-yl}-acetic acid;

[7-(5-benzyl-[1,2,3]triazol-1-yl)-4-fluoro-6,7,8,9-tetrahydropyrido[1,2-α]indol-10-yl]-acetic acid;

{4-fluoro-7-[5-(4-fluorobenzyl)-1H-[1,2,3]triazol-1-yl]-6,7,8,9-tetrahydropyrido[1,2-α]indol-10-yl}-acetic acid;

{(7R)-4-fluoro-7-[5-(4-fluorobenzyl)-1H-[1,2,3]triazol-1-yl]-6,7,8,9-tetrahydropyrido[1,2-a]-indol-10-yl}-acetic acid;

[3-(5-benzyl-[1,2,3]triazol-1-yl)-1,2,3,4-tetrahydro-carbazol-9-yl]-acetic acid;

{7-[4-(4-fluoro-phenyl)-[1,2,3]triazol-1-yl]-6,7,8,9-tetrahydropyrido[1,2-α]indol-10-yl}-acetic acid;

{7-[4-(4-methanesulfonylamino-butyl)-[1,2,3]triazol-1-yl]-6,7,8,9-tetrahydropyrido[1,2-α]indol-10-yl}-acetic acid;

{7-[4-(1-hydroxy-2-methyl-propyl)-[1,2,3]triazol-1-yl]-6,7,8,9-tetrahydropyrido[1,2-α]indol-10-yl}-acetic acid;

{7-[4-(1-hydroxy-1-phenyl-ethyl)-[1,2,3]triazol-1-yl]-6,7,8,9-tetrahydropyrido[1,2-α]indol-10-yl}-acetic acid;

[7-(4-phenoxymethyl-[1,2,3]triazol-1-yl)-6,7,8,9-tetrahydropyrido[1,2-α]indol-10-yl]-acetic acid;
{7-[4-(4-methanesulfonyl-phenyl)-[1,2,3]triazol-1-yl]-6,7,8,9-tetrahydropyrido[1,2-α]indol-10-yl}-acetic acid;
(7-{4-[4-(1-hydroxy-1-methyl-ethyl)-phenyl]-[1,2,3]triazol-1-yl}-6,7,8,9-tetrahydropyrido[1,2-α]indol-10-yl)-acetic acid;
{7-[4-(4-trifluoromethyl-phenyl)-[1,2,3]triazol-1-yl]-6,7,8,9-tetrahydropyrido[1,2-α]indol-10-yl}acetic acid;
[7-(4-naphthalen-1-yl-[1,2,3]triazol-1-yl)-6,7,8,9-tetrahydropyrido[1,2-α]indol-10-yl]-acetic acid;
{7-[4-(4-dimethylamino-phenyl)-[1,2,3]triazol-1-yl]-6,7,8,9-tetrahydropyrido[1,2-α]indol-10-yl}-acetic acid;
{7-[5-(4-fluoro-phenyl)-[1,2,3]triazol-1-yl]-6,7,8,9-tetrahydropyrido[1,2-α]indol-10-yl}-acetic acid;
[7-(5-phenoxymethyl-[1,2,3]triazol-1-yl)-6,7,8,9-tetrahydropyrido[1,2-α]indol-10-yl]-acetic acid;
(7-{5-[(4-bromophenyl)-hydroxy-methyl]-[1,2,3]triazol-1-yl}-6,7,8,9-tetrahydropyrido[1,2-α]indol-10-yl)-acetic acid;
4-[3-(10-carboxymethyl-6,7,8,9-tetrahydropyrido[1,2-α]indol-7-yl)-3H-[1,2,3]triazol-4-yl]-piperidine-1-carboxylic acid tert-butyl ester;
[7-(5-cyclohexyl-[1,2,3]triazol-1-yl)-6,7,8,9-tetrahydropyrido[1,2-α]indol-10-yl]-acetic acid;
{7-[5-(9-hydroxy-9H-fluoren-9-yl)-[1,2,3]triazol-1-yl]-6,7,8,9-tetrahydropyrido[1,2-α]indol-10-yl}-acetic acid;
(7-{5-[1-(4-fluorophenyl)-vinyl]-[1,2,3]triazol-1-yl]-6,7,8,9-tetrahydropyrido[1,2-α]indol-10-yl)-acetic acid;
(7-{(R)-5-[bis-(4-fluorophenyl)-hydroxy-methyl]-[1,2,3]triazol-1-yl}-6,7,8,9-tetrahydropyrido[1,2-α]indol-10-yl)-acetic acid;
{(R)-7-[5-(4-fluorobenzyl)-[1,2,3]triazol-1-yl]-6,7,8,9-tetrahydropyrido[1,2-α]indol-10-yl}-acetic acid;
{(R)-7-[5-(1-phenylethyl)-[1,2,3]triazol-1-yl]-6,7,8,9-tetrahydropyrido[1,2-α]indol-10-yl}-acetic acid;
((R)-7-{5-[bis-(4-fluorophenyl)-methyl]-[1,2,3]triazol-1-yl}-6,7,8,9-tetrahydropyrido[1,2-α]indol-10-yl)-acetic acid;
((R)-7-{5-[1-(4-fluorophenyl)-1-hydroxyethyl]-[1,2,3]triazol-1-yl}-6,7,8,9-tetrahydropyrido[1,2-α]indol-10-yl)-acetic acid;
{4-fluoro-7-[5-(1-phenyl-ethyl)-[1,2,3]triazol-1-yl]-6,7,8,9-tetrahydropyrido[1,2-α]indol-10-yl}-acetic acid;
{7-[5-(3,4-difluorobenzyl)-1H-1,2,3-triazol-1-yl]-4-fluoro-6,7,8,9-tetrahydropyrido[1,2-α]indol-10-yl}acetic acid;
{7-[5-(4-chlorobenzyl)-1H-1,2,3-triazol-1-yl]-4-fluoro-6,7,8,9-tetrahydropyrido[1,2-α]indol-10-yl}acetic acid; and
{7-[5-(2,2,2-trifluoro-1-hydroxy-1-phenylethyl)-1H-1,2,3-triazol-1-yl]-6,7,8,9-tetrahydropyrido[1,2-α]indol-10-yl}acetic acid.

The invention also encompasses pharmaceutical compositions containing a compound of formula I, and methods for treatment or prevention of prostaglandin mediated diseases using compounds of formula I.

The invention is described using the following definitions unless otherwise indicated.

The term "halogen" or "halo" includes F, Cl, Br, and I.

The term "alkyl" refers to linear or branched alkyl chains having the indicated number of carbon atoms. Non-limiting examples of alkyl groups include methyl, ethyl, propyl, isopropyl, butyl, s- and t-butyl, pentyl, hexyl, and the like.

"Haloalkyl" means an alkyl group as described above wherein one or more hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Alkoxy" means alkoxy groups of a linear or branched alkyl chain having the indicated number of carbon atoms. $C_{1-6}$alkoxy, for example, includes methoxy, ethoxy, propoxy, isopropoxy, and the like.

"Aryl" means a 6-14 membered carbocyclic aromatic ring system comprising 1-3 benzene rings. If two or more aromatic rings are present, then the rings are fused together, so that adjacent rings share a common bond. Examples include phenyl and naphthyl. "Optionally substituted aryl" means an aryl group that is unsubstituted or substituted as defined.

The term "heteroaryl" (Het) as used herein represents a 5-10 membered aromatic ring system containing one ring or two fused rings, 1-4 heteroatoms, selected from O, S and N. Het includes, but is not limited to, furanyl, imidazolyl, isoxazolyl, isothiazolyl, oxadiazolyl, oxazolyl, pyrazolyl, pyridyl, pyrrolyl, tetrazolyl, thiazolyl, thiadiazolyl, thienyl, triazinyl, triazolyl, 1H-pyrrole-2,5-dionyl, 2-pyrone, 4-pyrone, pyrrolopyridine, furopyridine and thienopyridine. "Optionally substituted heteroaryl" means a heteroaryl group that is unsubstituted or substituted as defined.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s).

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I may be obtained by stereospecific synthesis using optically pure starting materials, intermediates or reagents of known configuration.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, Ia, Ib, Ic and Id, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates Utilities The ability of compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastatic tumor growth and hence can be used in the treatment of cancer. Compounds of formula I may also be of use in the treatment and/or prevention prostaglandin-mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be used in the treatment of dysmenorrhea, premature labor and eosinophil related disorders. More particularly compounds of formula I are antagonists of prostaglandin D2 receptor, CRTH2.

Accordingly, another aspect of the invention provides a method of treating or preventing a prostaglandin mediated disease comprising administering to a mammalian patient in need of such treatment a compound of formula I in an amount which is effective for treating or preventing said prostaglandin mediated disease. Prostaglandin mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases; congestive heart failure; diseases or conditions requiring a treatment of anti-coagulation such as post-injury or post surgery treatment; inflammation; gangrene; Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly the disease to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is nasal congestion, rhinitis including allergic and perennial rhinitis, and asthma including allergic asthma.

In another embodiment of the present invention is a method of treating or preventing a prostaglandin D2-mediated disease comprising administering to a mammalian patient in need of such treatment a compound of formula I in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, including allergic asthma, in a patient in need of such treatment which comprises administering to said patient a therapeutically effective amount of a compound of formula I.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

In one embodiment the medicinal preparation is adapted for use with a pressurized metered dose inhaler which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs) as the use of chlorofluorocarbons (known also as Freons or CFCs) is being phased out. In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler. The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agents particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin mediated diseases comprising a therapeutically effective amount of a compound of formula I and one or more other therapeutic agents. Suitable therapeutic agents for combination therapy with a compound of formula I include: (1) a DP receptor antagonist such as S-5751; (2) a corticosteroid such as triamcinolone acetonide, budesonide, beclomethasone, mometasone furoate, fluticasone propionate, and ciclesonide; (3) a β-agonist such as salmeterol, formoterol, terbutaline, metaproterenol, albuterol and the like; (4) a leukotriene modifier, including a leukotriene receptor antagonist such as montelukast, zafirlukast, pranlukast, or a lipooxygenase inhibitor including 5-lipooxygenase inhibitors and FLAP (5-lipooxygenase activating protein) inhibitors such as zileuton; (5) an antihistamine such as bromopheniramine, chlorpheniramine, dexchlor-pheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant including phenylephrine, phenylpropanolamine, pseudophedrine, oxymetazoline, ephinephrine, naphazoline, xylometazoline, propylhexedrine, or levodesoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) nonsteroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors such as celecoxib and rofecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide, tiotropium bromide, trospium chloride, aclidinium bromide and glycopyrrolate including R,R-glycopyrrolate), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D$_2$ mediated diseases comprising: administration to a patient in need of such treatment a non-toxic therapeutically effective amount of a compound of formula I, optionally co-administered with one or more of such ingredients as listed immediately above.

Methods of Synthesis

Compounds of Formula I of the present invention can be prepared according to the synthetic routes outlined in the following scheme(s) and by following the methods described herein. Abbreviations used include: Ac=Acetyl; Bu=Butyl; COD=1,5-cyclooctadiene; Cp*= pentamethylcyclopentadienyl; CPME=Cyclopropyl methyl ether; DCM=Dichloromethane; DIPEA=Diisopropylethylamine; DMF=Dimethylformamide; EA/EtOAc=Ethyl acetate; Et=Ethyl; Hex=Hexane; HMDS=Hexamethyldisilazane; IPA=Isopropanol; IPAc=Isopropyl acetate; iPr=Isopropyl; Me=Methyl; Ms=Methanesulfonyl (mesyl); MTBE=Methyl t-butyl ether; Pr=Propyl; RT=Room temperature; t-bu=Tertbutyl; TEA=Triethylamine; THF=Tetrahydrofuran; TMS=Trimethylsilyl; p-TSA=p-toluenesulfonic acid As shown in Scheme 1, substituted azides VIII can be prepared in seven consecutives steps. Condensation of 4-oxopimelate I with substituted hydrazines II in refluxing toluene results in the ethyl ester intermediates III. Upon treatment of III with methanesulfonic acid in propanol the corresponding indoles IV can be obtained. Regioselective addition of the anion of trimethylsulfonium iodide onto the ester at the 2-position of the indole provides ylides V. Cyclisation of V in the presence of a catalytic amount of chloro(1,5-cyclooctadiene)iridium(I) dimer affords the desired ketoindoles VI. Conversion of the ketone moiety to the azide VIII can be carried out via a standard 3 step protocol involving reduction with sodium borohydride, mesylation with methanesulfonyl chloride and displacement with sodium azide.

Scheme 1: Synthesis of azides

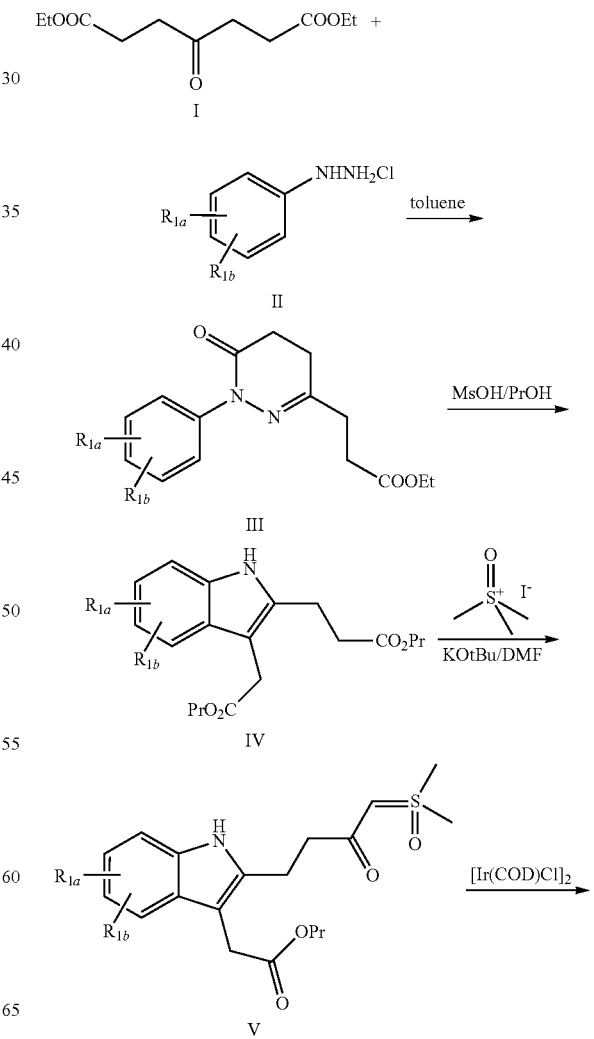

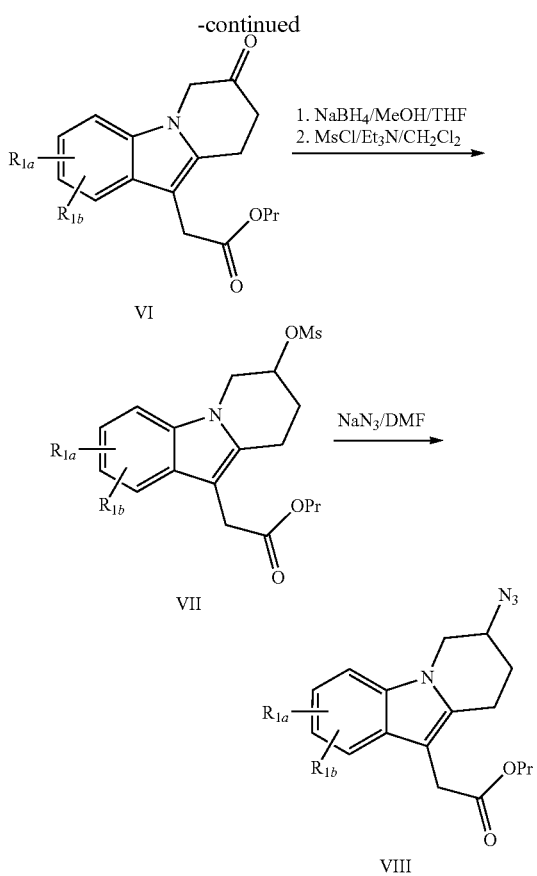

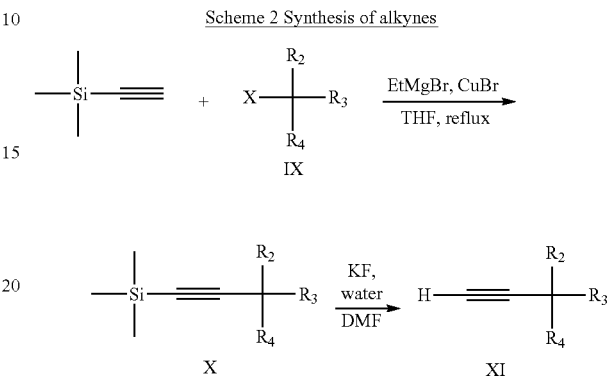

Non-commercial alkynes can be prepared by reaction of trimethylsilylacetylene and the corresponding benzyl halide IX using ethylmagnesium bromide and copper bromide (Scheme 2, *Gazz. Chim. Ital.* 1990, 120, 783). Removal of the TMS group in X can be accomplished by using aqueous KF in DMF to afford the desired substituted alkynes XI.

Triazole such as XIII and XV can be prepared using Click chemistry. Cycloaddition (3+2) of azides VIII and alkynes XI in presence of copper iodide affords exclusively the 1,4-triazole XII (*Angew. Chem. Int. Ed.* 2002, 41, 2596). 1,5-Triazole such as XIV can be prepared using a ruthenium complex (*J. Am. Chem. Soc.* 2005, 127, 15998). Hydrolysis of XII or XIV in aqueous base yields the final product XIII or XV.

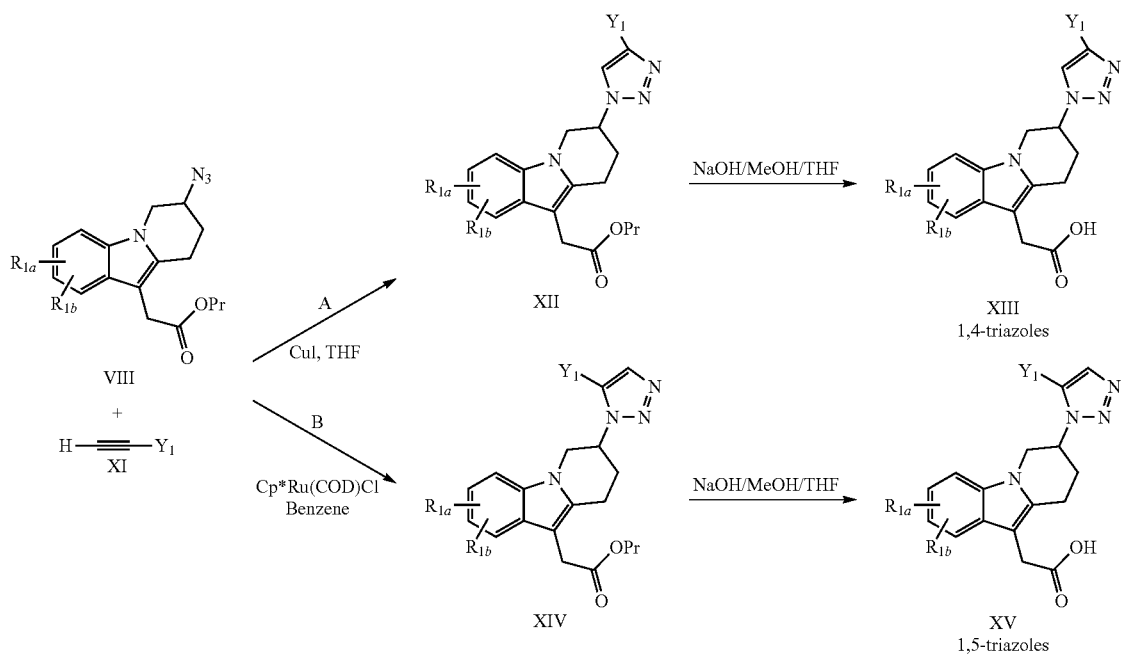

Scheme 3: Synthesis of 1,4-triazoles (Part A) and 1,5-triazoles (Part B)

Ketone XVI was previously reported in *J. Med. Chem.* 2005, 48, 897. Conversion of the ketone moiety XVI to the azide XVIII can be carried out via a standard 3 step protocol involving reduction with sodium borohydride, mesylation with methanesulfonyl chloride and displacement with sodium azide. Azide XVIII can be coupled with alkyne XI using either copper or ruthenium to obtain triazole XIX. Standard hydrolysis furnished the desired acid XX.

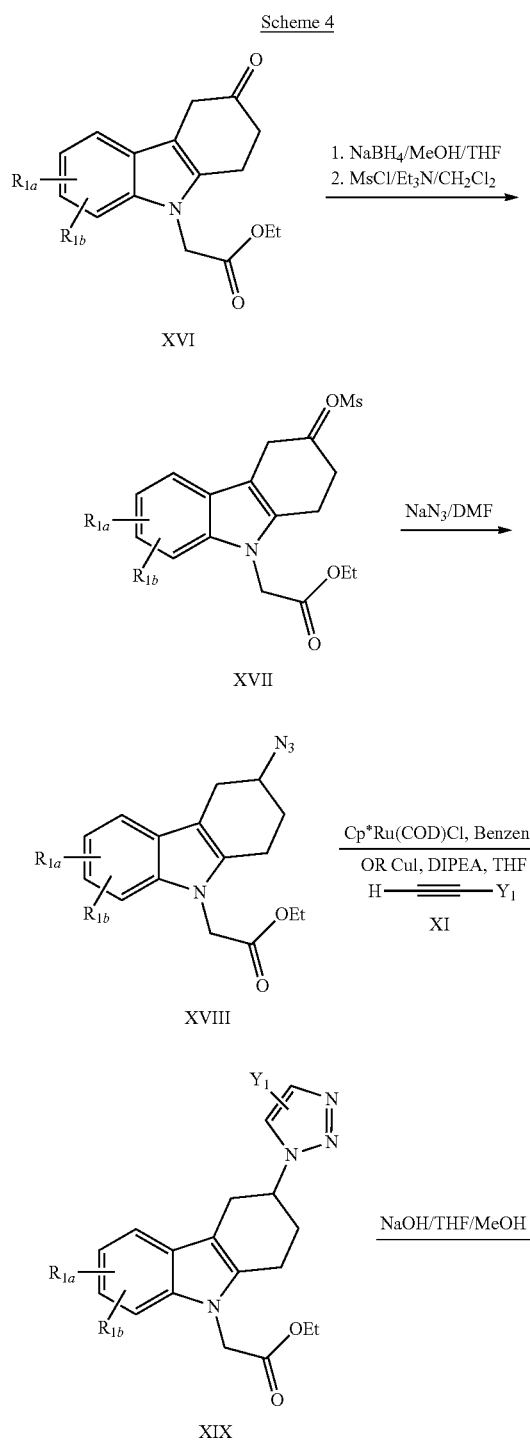

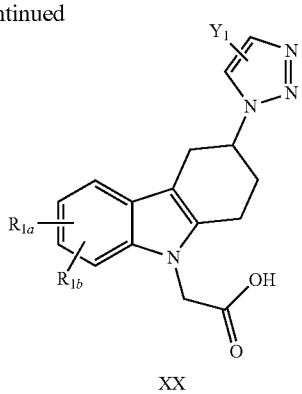

Alternative route to non-commercial alkynes involves using Sonogashira conditions to provide TMS-alkyne which can be deprotected to acetylene XXII by using catalytic amount of tetramethylammonium fluoride tetrahydrate buffered with acetic acid. Internal alkynes can be prepared by alkylation of the terminal alkyne XXIII with methyl iodide to provide alkyne XXIV (Scheme 5, Knobloch, K.; Keller, M.; Eberbach, W. *Eur. J. Org. Chem.* 2001, 3313-23332). Geminal dimethyl α-substituted alkynes can be prepared through deprotonation of ester XXV with sodium hydride followed by alkylation with methyl iodide. Reduction of the ester XXVI, followed by oxidation under Swern conditions yields the aldehyde XXVII. Treatment with Bestmann's reagent provides the desired geminal dimethyl substituted alkyne XXVIII.

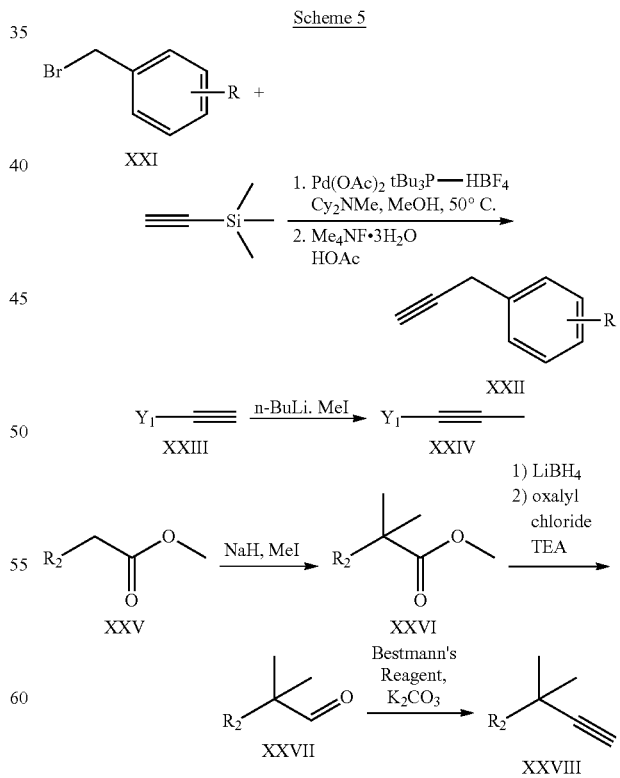

Indole XXXI can be prepared via ketal (XXIX) and imine (XXX) formation, followed by Heck cyclization and ylide formation. Iridium-catalyzed cyclization provided ketone XXXII. The conversion of ketone to chiral alcohol XXXIII can be accomplished via enzyme reduction to install the required stereocenter.

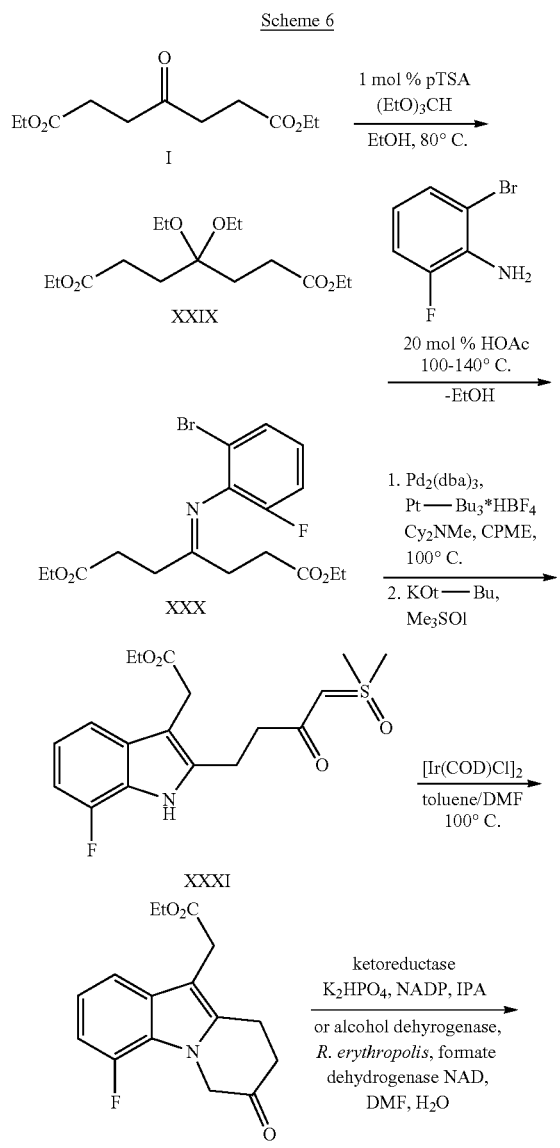

Scheme 6

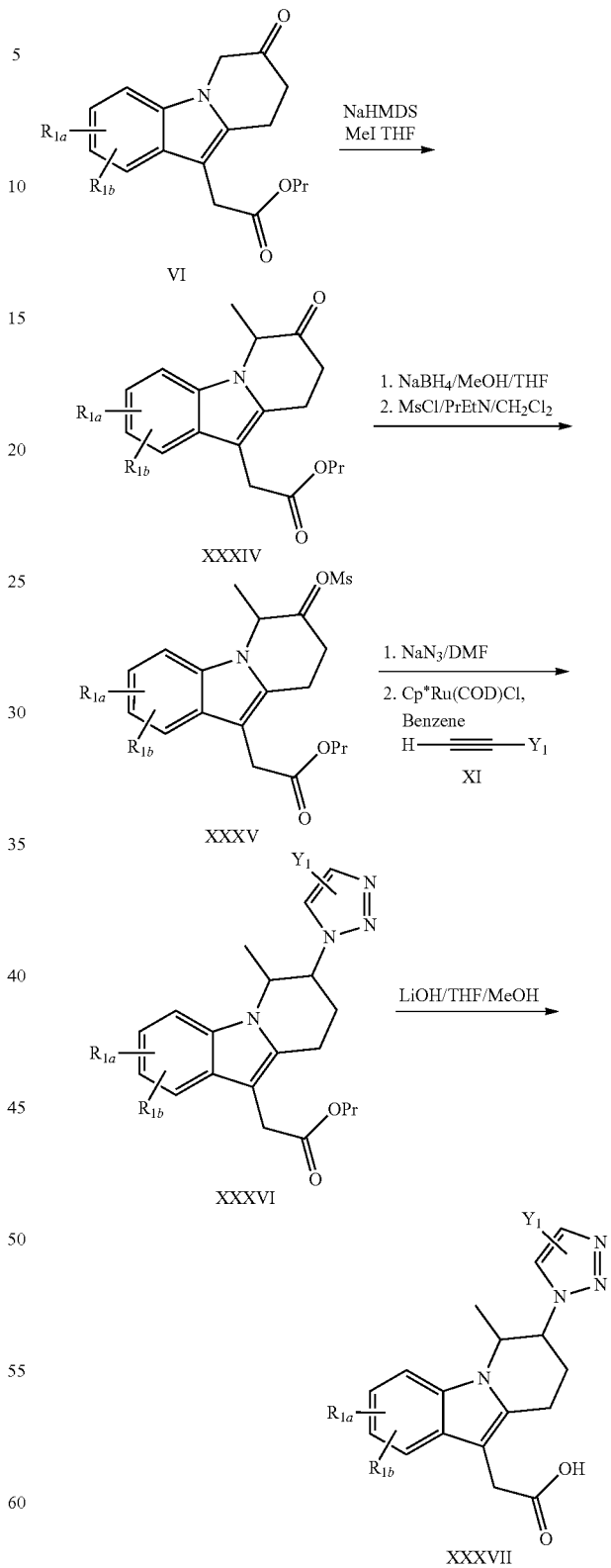

Scheme 7

Alkylation of the ketone VI with iodomethane provided the substituted ketone XXXIV. Conversion of the ketone moiety XXXIV to triazole XXXVII was carried out following a protocol similar to the none-methylated ketone shown in Scheme 1 and Scheme 3.

Disubstituted alkynes can also be coupled with azide VIII using a ruthenium catalyst to provide a regioisomeric mixture of 1,4,5-triazoles. Following separation of isomers and hydrolysis of the corresponding esters, carboxylic acids XXXVIII and XXXIX were obtained.

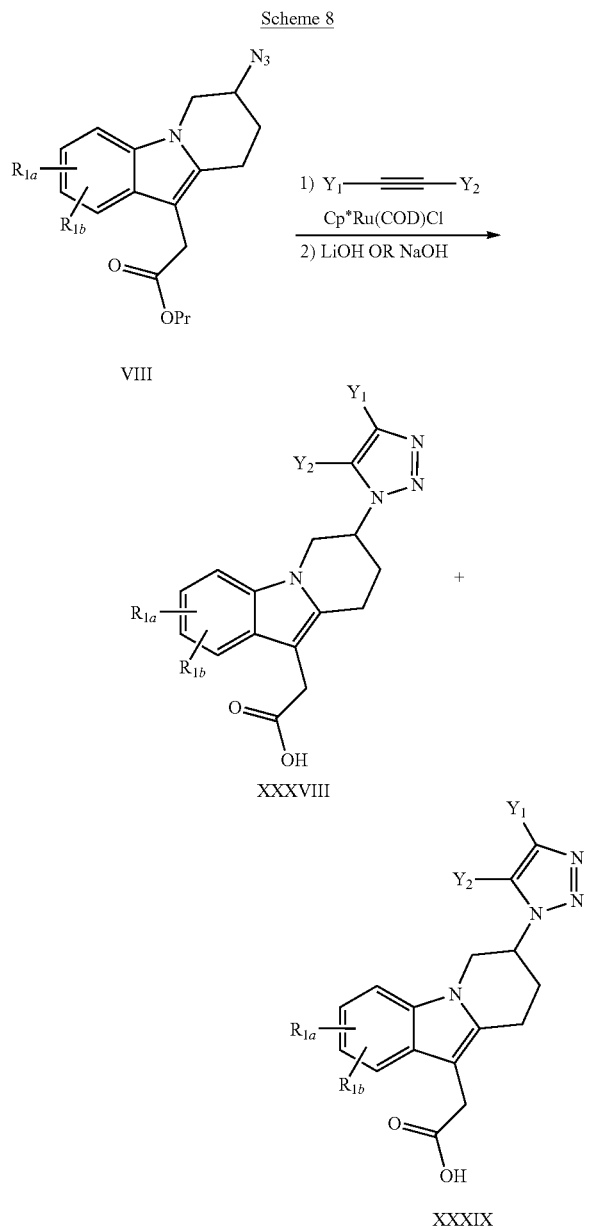

Compounds of formula I can be prepared according to the procedures described in the Schemes and Examples herein, using appropriate materials and are further exemplified by the following specific examples. The compounds exemplified are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

EXAMPLE 1

[7-(4-Benzyl-[1,2,3]triazol-1-yl)-6,7,8,9-tetrahydro-pyrido[1,2-α]indol-10-yl]-acetic acid

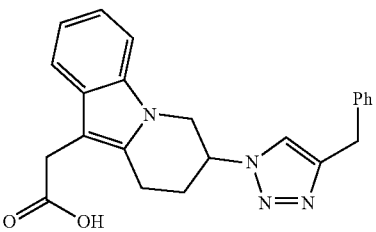 [SMILES: O=C(O)Cc1c2n(c3ccccc13)CC(n1cc(Cc3ccccc3)nn1)CC2]

Step 1: Propyl [7-(4-benzyl-1H-1,2,3-triazol-1-yl)-6,7,8,9-tetrahydropyrido[1,2-α]indol-10-yl]acetate To a stirred solution of propyl (7-azido-6,7,8,9-tetrahydro-pyrido[1,2-α]indol-10-yl)acetate (1 eq) (Synthesis described in WO07019675 A1) and prop-2-yn-1-ylbenzene (2 eq) in tetrahydrofuran (THF) (0.1M) at room temperature was added diisopropylethylamine (DIPEA) (5 eq) and CuI (5 eq). The reaction mixture was stirred overnight then quenched with $NH_4Cl$ sat and extracted with ethyl acetate (EA), washed with brine, dried over $Na_2SO_4$ and evaporated. Purification by combi-flash EA/Hex 0-100% afforded the desired compound which was used directly for next step.

Step 2

To a stirred solution of propyl [7-(4-benzyl-1H-1,2,3-triazol-1-yl)-6,7,8,9-tetrahydropyrido[1,2-α]indol-10-yl]acetate (1 eq) in THF/MeOH (2:1, 0.1M) at room temperature was added a 2M solution of potassium hydroxide (10 eq) The reaction mixture was stirred at room temperature for 2 h then quenched by adding HCl 10% until acidic pH and diluted with dichloromethane (DCM). Filtration through a phase separator followed by evaporation afforded the desired product as a white solid. $^1$H NMR (400 MHz, DMSO-$d_6$): δ 12.13 (s, 1 H), 8.05 (s, 1 H), 7.46 (d, 1 H), 7.40 (d, 1 H), 7.34-7.17 (m, 5 H), 7.12-7.00 (m, 2 H), 5.35-5.18 (m, 1 H), 4.67 (dd, 1 H), 4.32 (dd, 1 H), 4.02 (s, 2 H), 3.69-3.50 (m, 2 H), 3.07-2.92 (m, 2 H), 2.52-2.30 (m, 2 H). MS (+ESI) m/z: 387.2.

EXAMPLE 2

{7-[4-(4-Methoxy-phenyl)-[1,2,3]triazol-1-yl]-6,7,8,9-tetrahydropyrido[1,2-α]indol-10-yl}-acetic acid

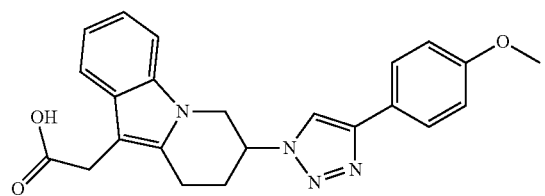 [SMILES: COc1ccc(-c2cn(C3CCc4c(CC(=O)O)c5ccccc5n4C3)nn2)cc1]

The title compound was prepared using analogous procedures described in EXAMPLE 1 from propyl (7-azido-6,7,8,9-tetrahydropyrido[1,2-α]indol-10-yl)acetate and 1-ethynyl-4-methoxybenzene. $^1$H NMR (400 MHz, DMSO-d$_6$): δ 12.14 (s, 1 H), 8.67 (s, 1 H), 7.78 (d, 2 H), 7.48 (d, 1 H), 7.42 (d, 1 H), 7.13-6.99 (m, 4 H), 5.40-5.30 (m, 1 H), 4.74 (dd, 1 H), 4.40 (dd, 1 H), 3.80 (s, 3 H), 3.61 (s, 2 H), 3.12-3.01 (m, 2 H). MS (+ESI) m/z: 403.1.

EXAMPLE 3

[7-(5-Benzyl-[1,2,3]triazol-1-yl)-6,7,8,9-tetrahydropyrido[1,2-α]indol-10-yl]-acetic acid

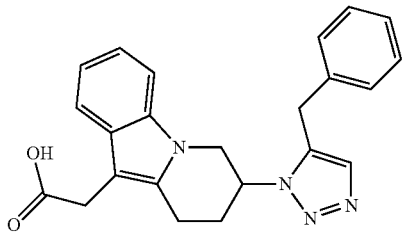 [SMILES: O=C(O)Cc1c2n(c3ccccc13)CC(n1nncc1Cc1ccccc1)CC2]

Step 1: Propyl [7-(5-benzyl-1H-1,2,3-triazol-1-yl)-6,7,8,9-tetrahydropyrido[1,2-α]indol-10-yl]acetate To a stirred solution of propyl (7-azido-6,7,8,9-tetrahydropyrido[1,2-α]indol-10-yl)acetate (Synthesis described in WO07019675 A1) and prop-2-yn-1-ylbenzene (1.5 eq) in benzene (0.3M) at room temperature was added chloro(1,5-cyclooctadiene)-(pentamethylcyclopentadienyl)ruthenium (II) (0.1 eq). The reaction mixture was flushed with nitrogen then heated to 80° C. overnight, cooled to room temperature, filtered through silica gel, washed with EtOAc and concentrated. The residue was purified by column chromatography on silica gel eluting with EtOAc/Hexane (0 to 50%) to give the desired racemic esters which were resolved by SFC using a 10×250 mm Chiralpak AD column eluting with 40% MeOH at 5 mL/min at ISOBAR and 254 nm (retention times=7.5 and 9.8 min).

Step 2

The resulting chiral esters (1 eq) (retention times=7.5 and 9.8 min) were hydrolyzed separately at room temperature using a 2M solution of potassium hydroxide (10 eq) in THF/MeOH (2:1, 0.1M). The reaction mixture was stirred at room temperature for 2 h then quenched by adding HCl 10% until acidic pH and diluted with DCM. Filtration through a phase separator followed by evaporation afforded EXAMPLE 3.1 and 3.2 respectively. $^1$H NMR data is for EXAMPLE 3.1: $^1$H NMR (400 MHz, DMSO-d$_6$): δ 12.14 (s, 1 H), 7.57 (s, 1 H), 7.46 (d, 1 H), 7.43-7.28 (m, 2 H), 7.40-7.22 (m, 3 H), 7.29-7.19 (m, 1 H), 7.05 (t, 2 H), 5.14 (s, 1 H), 4.53-4.28 (m, 1 H), 4.28 (s, 2 H), 4.18 (t, 1 H), 3.81-3.36 (m, 2 H), 3.09 (d, 1 H), 3.02-2.73 (m, 1 H), 2.50-2.07 (m, 1 H), 2.22-1.94 (m, 1 H). MS (+ESI) m/z: 387.2.

EXAMPLE 4

(7-{5-[(2,6-dichlorophenoxy)methyl]-1H-1,2,3-triazol-1-yl}-6,7,8,9-tetrahydropyrido[1,2-α]indol-10-yl)acetic acid

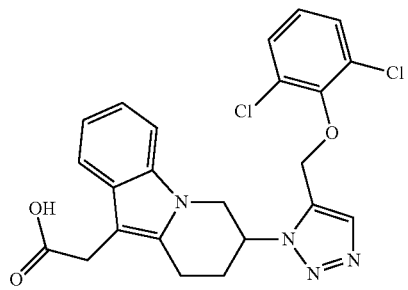 [SMILES: O=C(O)Cc1c2n(c3ccccc13)CC(n1nncc1COc1c(Cl)cccc1Cl)CC2]

The title compound was prepared using analogous procedures described in EXAMPLE 3 from propyl (7-azido-6,7,8,9-tetrahydropyrido[1,2-α]indol-10-yl)acetate and 2,6-dichlorophenyl prop-2-yn-1-yl ether. $^1$H NMR (400 MHz, DMSO-d$_6$): δ 12.14 (s, 1 H), 7.91 (s, 1 H), 7.54 (d, 2 H), 7.49 (d, 1 H), 7.35 (d, 1 H), 7.25 (t, 1 H), 7.11-7.00 (m, 2 H), 5.48-5.32 (m, 3 H), 4.78 (dd, 1 H), 4.37 (t, 1 H), 3.62 (d, 2 H), 3.43-3.34 (m, 1 H), 3.24-3.09 (m, 1 H), 3.09-2.97 (m, 1 H). MS (+ESI) m/z: 471.1.

EXAMPLE 5

(7-{5-[1-(4-Fluoro-phenyl)-1-hydroxy-ethyl]-[1,2,3]triazol-1-yl}-6,7,8,9-tetrahydropyrido[1,2-α]indol-10-yl)-acetic acid

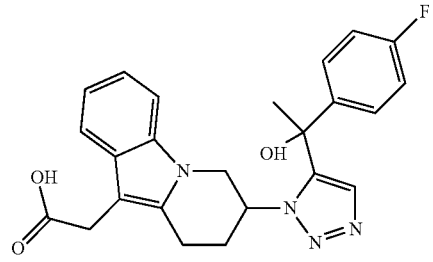 [SMILES: CC(O)(c1ccc(F)cc1)c1cnnn1C1CCc2c(CC(=O)O)c3ccccc3n2C1]

The title compound was prepared using analogous procedures described in EXAMPLE 3 from propyl (7-azido-6,7,8,9-tetrahydropyrido[1,2-α]indol-10-yl)acetate and 2-(4-fluorophenyl)but-3-yn-2-ol. Separation of the resulting diastereoisomers was performed at the ester stage by flash chromatography using a gradient of 10-70% EA/Hex afforded two enantiomeric mixtures. The faster eluting enantiomeric mixture was resolved on chiral HPLC using a 50×400 mm Chiralcel OD column eluting with 8% iPrOH, 8% EtOH, 83.75% Hexanes and 0.25% Et$_3$N at 60 mL/min and 254 nm. The resulting esters (retention times=18.4 and 22.1 min) were hydrolyzed separately in THF/MeOH (2:1, 0.1M) at room temperature using 1M solution of sodium hydroxide (10 eq). The reaction mixture was stirred at room temperature for 2 h then quenched by adding HCl 10% until acidic pH and diluted with DCM. Filtration through a phase separator followed by evaporation afforded the desired EXAMPLE 5.1 and 5.2 respectively. The slower eluting enantiomeric mixture was resolved on chiral HPLC using a 50×400 mm Chiralcel OD eluting with 30% iPrOH, 70%

Hexanes at 60 mL/min and 254 nm. The resulting esters (retention times=18.3 and 34 min) were hydrolyzed in a similar fashion as described above to afford EXAMPLE 5.3 and 5.4 respectively. $^1$H NMR data is for EXAMPLE 5.1: $^1$H NMR (400 MHz, DMSO-d$_6$): δ 12.13 (s, 1 H), 7.97 (s, 1 H), 7.45 (d, 1 H), 7.36 (dd, 2 H), 7.31 (d, 1 H), 7.20 (t, 2 H), 7.11-7.00 (m, 2 H), 6.68 (s, 1 H), 5.03 (s, 1 H), 4.54 (dd, 1 H), 4.24 (t, 1 H), 3.60-3.48 (m, 2 H), 3.01-2.91 (m, 1 H), 2.37-2.26 (m, 1 H), 2.02-1.93 (m, 1 H), 1.90 (s, 3 H), 1.36-1.24 (m, 1 H). MS (+ESI) m/z: 435.1.

EXAMPLE 6

{7-[5-(1-Phenyl-cyclopentyl)-[1,2,3]triazol-1-yl]-6,7,8,9-tetrahydropyrido[1,2-α]indol-10-yl}-acetic acid

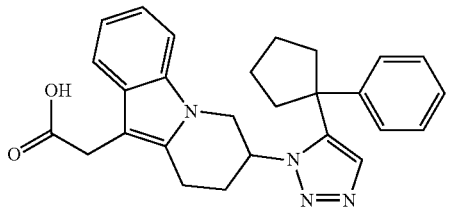 [SMILES: O=C(O)Cc1c2n(c3ccccc13)CC(n1nncc1C1(c3ccccc3)CCCC1)CC2]

The title compound was prepared using analogous procedures described in EXAMPLE 3 from (1-ethynylcyclopentyl)benzene and enantiomerically pure propyl (7-azido-6,7,8,9-tetrahydropyrido[1,2-α]indol-10-yl)acetate, prepared by resolution of the racemic azide on a 4.6×250 mm ChiralCel OD column eluting with 15% MeOH, 15% iPrOH, 69.75% Hexanes and 0.25% Et$_3$N at 1 mL/min and 254 nm. Retention times=10.3 and 11.5 min. EXAMPLE 6.1 and 6.2 were prepared from the chiral azide with the retention time of 10.3 and 11.5 min respectively. $^1$H NMR data of EXAMPLE 6.1: $^1$H NMR (400 MHz, DMSO-d$_6$): δ 12.13 (s, 1 H), 7.93 (s, 1 H), 7.42 (d, 1 H), 7.36 (dd, 2 H), 7.31-7.23 (m, 3 H), 7.13 (d, 1 H), 7.07-6.97 (m, 2 H), 4.59 (s, 1 H), 3.98-3.89 (m, 1 H), 3.58-3.46 (m, 2 H), 3.03-2.92 (m, 1 H), 2.29-2.20 (m, 1 H), 2.10-2.01 (m, 1 H), 1.54-1.43 (m, 1 H). MS (+ESI) m/z: 441.2.

EXAMPLE 7

[7-(5-Benzyl-[1,2,3]triazol-1-yl)-4-fluoro-6,7,8,9-tetrahydropyrido[1,2-α]indol-10-yl]-acetic acid

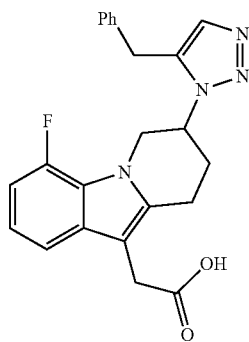 [SMILES: O=C(O)Cc1c2n(c3c(F)cccc13)CC(n1nncc1Cc1ccccc1)CC2]

Step 1: Ethyl 3-[1-(2-fluorophenyl)-6-oxo-1,4,5,6-tetrahydropyridazin-3-yl]propanoate In a flask equipped with a Dean-Stark trap, 2-fluorohydrazine hydrochloride (1 eq) and diethyl 4-oxopimelate (1 eq) were combined in toluene (1M). The suspension was aged 24 h at reflux. The reaction mixture was cooled to room temperature and concentrated under vacuum. The crude product was purified on a plug of silica gel eluting with EtOAc/Hexane (10 to 50%) to afford the desired material as an orange-brown oil which was used as such in the next step.

Step 2: Propyl 3-[7-fluoro-3-(2-oxo-2-propoxyethyl)-1H-indol-2-yl]propanoate

Methanesulfonic acid (1.2 eq) was added to a stirred solution of ethyl 3-[1-(2-fluorophenyl)-6-oxo-1,4,5,6-tetrahydropyridazin-3-yl]propanoate (1 eq) in n-propanol (1M). The mixture was heated for 48 h at 80° C. The mixture was cooled to room temperature and neutralized with an aqueous solution of sodium hydroxide (1.2 eq) and extracted with methyl t-butyl ether (MTBE). The organic layer was dried over sodium sulfate and concentrated. The residue was purified by on a short plug of silica gel, eluting with EtOAc/Hexane (0 to 60% in 30 min) to give the desired material as a brown oil.

Step 3: Propyl (2-{4-[dimethyl(oxido)-1-sulfanylidene]-3-oxobutyl}-7-fluoro-1H-indol-3-yl)acetate Trimethylsulfoxonium iodide (2 eq) was partially dissolved in THF (9M) and a solution of potassium t-butoxide in THF (2.4 eq) was added. The mixture was heated to 67° C. for 2 h, and then cooled to 0° C. To the cooled solution was added a solution of propyl 3-[7-fluoro-3-(2-oxo-2-propoxyethyl)-1H-indol-2-yl]propanoate (1 eq) in THF (5M) over 15 min. The mixture was allowed to warm to room temperature and stirred for 24 h. The reaction mixture was poured into a mixture of water and EtOAc, and the layers were cut. The aqueous layer was back extracted with EtOAc. The combined organic layers were washed successively with a saturated solution of NaHCO$_3$ and brine, dried (MgSO$_4$), filtered and concentrated to afford the desired material as an orange-brown solid which was used as such in the next step.

Step 4: Propyl (4-fluoro-7-oxo-6,7,8,9-tetrahydropyrido[1,2-α]indol-10-yl)acetate A degassed solution of propyl (2-{-4-[dimethyl(oxido)-1-sulfanylidene]-3-oxobutyl}-7-fluoro-1H-indol-3-yl)acetate (1 eq) in dimethylformamide (DMF) (0.2M) was added over 15 min using a cannula to the preheated (105° C.) degassed solution of chloro(1,5-cyclooctadiene)iridium(I) dimer (0.02 eq) in toluene (0.01M). The mixture was aged at 105° C. for 45 min, cooled to room temperature and poured onto brine and diluted with Et$_2$O. The layers were separated and the organic layer was washed again with brine. The organic layer was dried (Na$_2$SO$_4$), filtered and concentrated under reduced pressure. The residue was purified by column chromatography on silica gel eluting with EtOAc/Hexane (0 to 30% in 30 min) to give the desired material as a yellow oil.

Step 5: Propyl {4-fluoro-7-[(methylsulfonyl)oxy]-6,7,8,9-tetrahydropyrido[1,2-α]indol-10-yl}acetate To a stirred solution of propyl (4-fluoro-7-oxo-6,7,8,9-tetrahydropyrido[1,2-α]indol-10-yl)acetate (1 eq) and MeOH (3 eq) in THF (0.07M) at 0° C. was added NaBH₄ (1 eq). The reaction mixture was stirred at 0° C. for 60 min. A saturated solution of ammonium chloride and EtOAc was added and the layers were cut. The organic layer was washed with brine, dried (Na₂SO₄), filtered and concentrated to afford the desired alcohol as a solid which was used as such in the next step. To a stirred solution of crude alcohol (1 eq) in CH₂Cl₂ (0.33M) at 0° C. was added methanesulfonyl chloride (1.05 eq) followed by triethylamine (1.1 eq). The reaction mixture was stirred at 0° C. for 30 min., then overnight at room temperature. The reaction was quenched by addition of a solution of saturated NH₄Cl, extracted with ethyl acetate, washed with brine, dried and evaporated. The residue was purified by column chromatography on silica gel eluting with EtOAc/Hexane (0 to 100%) to give the desired material as a pale yellow oil.

Step 6: Propyl (7-azido-4-fluoro-6,7,8,9-tetrahydropyrido[1,2-α]indol-10-yl)acetate To a stirred solution of propyl {4-fluoro-7-[(methylsulfonyl)oxy]-6,7,8,9-tetrahydropyrido[1,2-α]indol-10-yl}acetate (1 eq) in DMF (0.15M) at 0° C. was added sodium azide (1.2 eq). The reaction mixture was stirred at 60° C. for 6 h. The reaction was quenched by addition of water and NH₄Cl, extracted with EtOAc, washed with water, brine, dried and evaporated. The residue was purified by column chromatography on silica gel eluting with EtOAc/Hexanes (0 to 50%) to give the desired material as a yellow oil.

Step 7: Propyl [7-(5-benzyl-1H-1,2,3-triazol-1-yl)-4-fluoro-6,7,8,9-tetrahydropyrido[1,2-α]indol-10-yl]acetate To a stirred solution of propyl (7-azido-4-fluoro-6,7,8,9-tetrahydropyrido[1,2-α]indol-10-yl)acetate (1 eq) and prop-2-yn-1-ylbenzene (1.5 eq) in benzene (0.3M) at room temperature was added chloro(1,5-cyclooctadiene)(pentamethylcyclopentadienyl)-ruthenium(II) (0.1 eq). The reaction mixture was flushed with nitrogen then aged at 80° C. for overnight, cooled to room temperature, filtered through silica gel, washed with EtOAc and concentrated. The residue was purified by column chromatography on silica gel eluting with EtOAc/Hexane (0 to 50%) to give the desired material as a brown oil. The racemic mixture was resolved by HPLC using a 50×400 mm Chiralpak AD column eluting with 15% MeOH, 15% EtOH, 69.75% Hexanes and 0.25% Et₃N at 50 mL/min and 254 nm to afford the desired chiral ester with retention time of 9.6 and 11.6 min respectively.

Step 8

The two chiral esters from Step 7 were saponified separately as follows. To a stirred solution of propyl [7-(5-benzyl-1H-1,2,3-triazol-1-yl)-4-fluoro-6,7,8,9-tetrahydropyrido[1,2-α]indol-10-yl]acetate (1 eq) in THF:MeOH (2:1 0.3M) at room temperature was added a 1M solution of sodium hydroxide (12 eq). The reaction mixture was stirred at room temperature for 2 h then quenched by adding HCl 10% until acidic pH and diluted with EtOAc. The layers were separated, and the aqueous phase was back-extracted with EtOAc. The combined organic fractions were dried (MgSO₄), filtered and the solvent was evaporated under reduced pressure to give the desired chiral acid 7.1 and 7.2 as white solids after coevaporation with ether/hexanes. ¹H NMR (400 MHz, acetone-d₆) δ 7.54 (s, 1 H), 7.23-7.39 (m, 5 H), 6.98 (dt, 1 H), 6.81 (dd, 1 H), 5.15-5.22 (m, 1 H), 4.71-4.76 (m, 1 H), 4.61 (m, 1 H), 4.37 (t, 2 H), 3.68 (q, 2 H), 3.21 (dt, 1 H), 2.94 (ddd, 1 H), 2.43 (dq, 1 H), 2.14-2.18 (m, 1 H). MS (+ESI) m/z: 405.2.

EXAMPLE 8

{4-Fluoro-7-[5-(4-fluoro-benzyl)-[1,2,3]triazol-1-yl]-6,7,8,9-tetrahydropyrido[1,2-α]indol-10-yl}-acetic acid

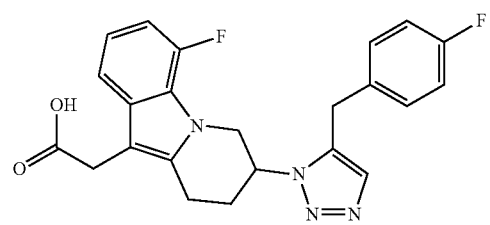 [SMILES: O=C(O)Cc1c2n(c3c(F)cccc13)CC(n1nncc1Cc1ccc(F)cc1)CC2]

The title compound was prepared using analogous procedures described in EXAMPLE 3 from propyl (7-azido-4-fluoro-6,7,8,9-tetrahydropyrido[1,2-α]indol-10-yl)acetate (EXAMPLE 7, Step 6) and 1-fluoro-4-prop-2-yn-1-ylbenzene obtained according to the following procedure (*Gazz. Chim. Ital.* 1990, 120, 783). To a mixture of ethynyltrimethylsilane (1 eq) in THF (0.6M) at room temperature was added ethylmagnesium bromide (1 eq). The mixture was stirred at room temperature for 30 min then copper bromide (I) (0.1 eq) was added. After stirring for 30 min, a 1M solution of 4-fluorobenzyl bromide (1 eq) in THF was added and the mixture was heated to reflux overnight. The reaction mixture was quenched by addition to a cold solution of NH₄Cl sat, stirred for 30 min then extracted with Et₂O, washed with brine, dried and evaporated. Purification by Combi-flash using a gradient of 0-100% EA/Hex afforded the desired TMS alkyne. The TMS alkyne was directly mixed with potassium fluoride (1.2 eq) in DMF (0.2M containing 1% water). The mixture was stirred at room temperature overnight then quenched by addition of HCl 3N, stirred for 1 h then extracted with pentanes, washed with NaHCO₃ sat, brine, dried and evaporated. Crude alkyne compound was used directly for click chemistry described in EXAMPLE 3. The resulting racemic esters were resolved by HPLC using a 4.6×250 mm Chiralpak AS column eluting with 60% EtOH, 39.75% Hexanes and 0.25% Et₃N at 0.8 mL/min and 254 nm. The resulting chiral esters (retention times=10.3 and 13.3 min) were hydrolyzed to afford EXAMPLE 8.1 and 8.2 respectively. ¹1-1 NMR of EXAMPLE 8.1: ¹H NMR (400 MHz, DMSO-d₆): δ 12.20 (s, 1 H), 7.55 (s, 1 H), 7.33 (dd, 2 H), 7.27 (d, 1 H), 7.17 (t, 2 H), 6.96 (td, 1 H), 6.85 (dd, 1 H), 5.23-5.09 (m, 1 H), 4.58 (dd, 1 H), 4.44 (dd, 1 H), 4.25 (s, 2 H), 3.65-3.52 (m, 2 H), 3.12-3.02 (m, 1 H), 2.89 (ddd, 1 H), 2.32-2.19 (m, 1 H), 2.14-2.02 (m, 1 H). MS (+ESI) m/z: 423.1.

EXAMPLE 8A

{(7R)-4-Fluoro-7-[5-(4-fluorobenzyl)-1H-[1,2,3]triazol-1-yl]-6,7,8,9-tetrahydropyrido[1,2-a]-indol-10-yl}-acetic acid

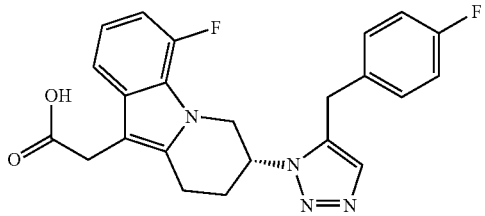 [SMILES: O=C(O)Cc1c2n(c3c(F)cccc13)C[C@H](n1nncc1Cc1ccc(F)cc1)CC2]

Step 1: Diethyl 4,4-diethoxyheptanedioate ("ketal")

To EtOH (27.8 L), triethyl orthoformate (9.26 L, 55.6 mol) and diethyl 4-oxopimelate (5.93 L, 27.8 mol) was added p-toluenesulfonic acid monohydrate (0.053 kg, 0.278 mol), and the reaction mixture was heated to 77.0° C. with stirring for 20 h. Heating was discontinued, and ethanol was removed by distillation under vacuum, starting with the batch at 63° C. The remaining orange ketal solution was dissolved in toluene (32 L) and transferred to a 100-L extractor that had been charged with 2% NaHCO$_3$ (24 L), with stirring.

The layers were separated and the toluene layer was washed with water (19.2 L), then transferred via in-line filter to a 50-L round bottom flask, attached to a heating mantle. Toluene was removed under vacuum, including an additional flush (5 L) for azeotropic removal of water. The ketal was isolated as a yellow oil.

Step 2: Diethyl 4[(2-bromo-6-fluorophenyl)imino]heptanedioate ("imine")

To the ketal of Step 1 (8.46 kg, 24.31 mol), were charged 2-bromo-6-fluoroaniline (2.509 L, 22.10 mol) and acetic acid (0.253 L, 4.42 mol) under nitrogen. The mixture was heated to 145° C. and ethanol was removed by distillation. The product was used in the next reaction.

Step 3: Ethyl 3-[3-(2-ethoxy-2-oxoethyl)-7-fluoro-1H-indol-2-yl]propanoate ("indole diester")

Cyclopropyl methyl ether (CPME, 27 L) was de-gassed for 20 minutes, then tris(dibenzylideneacetone)dipalladium(0) (0.504 kg, 0.551 mol) and tri-t-butylphosphonium tetrafluoroborate (0.639 kg, 2.203 mol), followed by CPME (3.2 L) were added. The mixture was de-gassed, and N-methyldicyclohexylamine (2.336 L, 11.01 mol) was added with continued de-gassing for 100 min.

The imine from Step 2 (8.86 kg, 22.03 mol) was dissolved in CPME (28 L) with active de-gassing. N-Methyldicyclohexylamine (7.01 L, 33.0 mol) was added, and the mixture was de-gassed for 75 min.

With continued nitrogen flow, the imine solution was transferred by vacuum to the catalyst solution, and the entire reaction vessel was rigorously de-gassed for 20 min. CPME (2.2 L) rinse, after de-gassing, was transferred to the reaction vessel under vacuum. The reaction mixture was de-gassed again for 35 min. and heated at ~108° C. for 18 h. The batch was washed 2×2N HCl (18 L), 1×5% NaHCO$_3$ (18 L), 1×H$_2$O (12 L).

The combined CPME layers were filtered via 2 in-line filters (1 normal, 1 carbon), and CPME was removed to a low volume by vacuum distillation, affording a dark yellow solution. Toluene (12 L) was charged and removed under vacuum to help flush out additional CPME. Heptane (18 L) was added, and the heterogeneous mixture was stirred, seeded with crystalline indole diester and allowed to continue cooling, but crystallization was not achieved.

Toluene (500 mL) and THF (5 L) were added to fully solubilize the batch; the reaction solution was cooled in a dry ice/acetone bath. At −6.8° C., the batch became slightly cloudy, a small amount of seed was added, and the batch turned over to crystals. Cooling was continued to −10 C over 30 minutes. At this temperature, heptane (30 L) was added, maintaining the temperature at <−6° C. The batch was cooled to −17 to −15° C. and aged for 1.5 hours. The batch was stirred an additional 2 hours at ~−17 C, then filtered cold with pumping at −19 to −18° C. A cold-heptane wash (12 L) was used to rinse the vessel and wash the sticky, yellow-orange crystals. The batch was dried under nitrogen and vacuum and the indole diester was isolated as a sticky yellow solid.

Step 4: Ethyl (2-{4-[dimethyl(oxido)-1-sulfanylidene]-3-oxobutyl}-7-fluoro-1H-indol-3-yl)acetate ("ylide")

To 1M potassium t-butoxide in THF (27 L) under N$_2$ at room temperature was added Me$_3$SOI (5.81 kg) portion-wise. The resulting suspension was heated to 66° C. for 2 hours. After cooling the reaction mixture to 30° C., a solution of the indole diester of Step 3 (5.35 kg) in THF (5 L) was charged over 10 min. Rinse with additional THF (2.5 L) was also transferred to the reaction vessel. The reaction mixture was heated to 60° C. for 2.5 hours.

After cooling the reaction mixture to 20° C., water (40 L) and EtOAc (20 L) were charged. The mixture was stirred at 20° C. for 30 min. The layers were separated, and additional water (15 L) was added to the aqueous layer to dissolve observed precipitate. The aqueous layer was back-extracted twice with EtOAc (20 L and 10 L). The combined organic layer was washed with sat. NaHCO$_3$ (30 L), then with 2 wt % aq. NaCl (20 L). The organic phase was filtered through two in-line filters (1 regular, 1 carbon). The filtrate was concentrated under reduced pressure and flushed with EtOAc (40 L) to a target volume of approximately 12 L. Heptane (24 L) was charged over 30 min. A yellow precipitate was observed. Additional EtOAc (500 mL) was charged to achieve a 3:1 volume ratio of heptane/EtOAc. The resulting suspension was aged at room temperature overnight, then filtered. The filter cake was washed with 25% EtOAc/heptane (32 L) and then dried at room temperature under vacuum and nitrogen to provide the ylide as a yellow solid.

Step 5: Ethyl (4-fluoro-7-oxo-6,7,8,9-tetrahydropyrido[1,2-α]indol-10-yl)acetate ("ketone")

[Ir(COD)Cl]$_2$ (46.9 g) was added to toluene (53 L) which had been sparged with N$_2$ overnight. After sparging with N$_2$ for an additional 50 min, the solution was heated to 100° C.

A solution of the ylide of Step 4 (1.74 kg) in DMF (7 L) (KF=1500 ppm) was sparged with N$_2$ for 1 h and then transferred to the above [Ir(COD)Cl]$_2$ solution at 100° C. over 1.5 hours. Rinse with degassed DMF (1 L) was transferred to the reaction vessel. After completion of the addition, the reaction mixture was kept at 100° C. for an additional 30 min.

After cooling to room temperature, the reaction mixture was washed with water (2×18 L), and the organic phase was filtered through 2 in-line filters (1 regular, 1 carbon). Silica gel (3.5 kg, 230-400 mesh, Grade 60) was charged, and the mixture was stirred at room temperature overnight. After filtration, the silica gel cake was washed with toluene (3×17 L). Two batches of this material were prepared and combined. The combined solution was filtered via two in-line filters (1 regular, 1 carbon), concentrated under reduced pressure and flushed with IPA (2×15 L) to a target volume of approximately 7 L. Toward the end of concentration, the product began to oil out as a red oil before crystallizing as a peach solid.

Water (15 L) was charged over 1 hour, and the resulting suspension was aged for 2 hour, filtered, and the filter cake washed with 1:2 IPA/water (15 L) and then dried at room temperature under vacuum and nitrogen to give the ketone as a peach.

Step 6: Ethyl[(7S)-4-fluoro-7-hydroxy-6,7,8,9-tetrahydropyrido[1,2-a]indol-10-yl]acetate ("alcohol")

$K_2HPO_4$ (0.604 kg, 3.47 mol) was dissolved in water (33 L) at room temperature, forming a 0.1M phosphate buffer. The pH was adjusted to 7.0 using 5N HCl (260 mL). The buffer was degassed by $N_2$ bubbling overnight. NADP (0.0422 kg, 0.055 mol) and CDX KRED P3H2 (Codex KRED Panel ketoreductase P3H2, available from Codexis, Inc., Redwood City, Calif., USA; 0.1925 kg, 5.23 mol) were dissolved in the pH 7.0 buffer at room temperature.

Isopropanol (14.5 L) was degassed by $N_2$ bubbling overnight. The ketone from Step 5 (1.61 kg, 5.23 mol) was added to the IPA and dissolved at 40-43° C. The warm solution was added to the enzyme solution, heated to 33-35° C. and aged overnight. After stirring for 20 hours, IPAc (31.1 L)) was added, and the mixture was stirred for 15 min. After 2 hours, the bottom aqueous was cut away, and the combined organic and emulsified rag layers were filtered through a bed of solka floc over 2-ply cotton cloth, washing with additional IPAc (11 L). The phases were separated, and the IPAc layer was washed with 1% brine (16 L) and water (16 L). The IPAc solution was filtered via two in-line filters (1 regular, 1 carbon) and flushed with additional IPAc (2×16 L) to a target volume of 11.5 L (10 L IPAc, 1.5 L alcohol).

Alternative Reduction:

Sodium formate (5.97 eq) and potassium phosphate, dibasic (1.3 eq) were dissolved in water (0.077M). The pH was adjusted to pH 7.0 using 6N HCl. Beta-Nicotinamide adenine dinucleotide (0.02 eq) was added and dissolved at RT. Then, alcohol dehydrogenase from *Rhodococcus Erythropolis* (50 wt %) and formate dehydrogenase (10%) were added and dissolved at room temperature using agitation. The temperature was set to 35° C. and the pH checked (7.0). Ethyl (4-fluoro-7-oxo-6,7,8,9-tetrahydropyrido[1,2-α]indol-10-yl)acetate was dissolved in DMF (0.69M). Half of this stock solution was added to the reactor. Three more fractions of the stock solution were charged every hour for 3 hours and DMF rinse was added last. The pH was 7.4 and was adjusted to 7.1 using 6N HCl.

At 21 hrs reaction time, the pH was 7.8. 6N HCl was added to adjust the pH to 7.3. The reaction was cooled to RT. Solka floc was added and mixed for ~3 hrs before filtration through a bed of solka floc. The aqueous was set aside and the filter cake washed 3 times with 2 L MTBE. This filtrate was allowed to settle in a separatory funnel, then the aqueous phase was cut and combined with the aqueous filtrate. The organic layer was washed with brine. The combined aqueous layer was extracted with MTBE and the phases allowed to settle overnight. The spent aqueous and the rag layer were discarded. The organic phase was washed with brine. The combined organic layers were concentrated and yielded desire indole product.

Step 7: Ethyl[(7S)-4-fluoro-7-methanesulfonyloxy-6,7,8,9-tetrahydropyrido[1,2-α]indol-10-yl]acetate ("mesylate")

A solution of alcohol of Step 6 (1.53 kg, 5.25 mol) in IPAc (9.95 L) was cooled to −20° C. $Et_3N$ (1.5 L, 10.76 mol) was added in one portion and the internal temperature was allowed to equilibrate to −10° C. MsCl (0.551 L, 7.07 mol) was added slowly over a period of 90 min to the reaction mixture; the internal temperature was maintained below 10° C. After an additional 5 min of stirring, additional MsCl (41 mL) was added and the reaction mixture was stirred for 15 min., cooled to −2° C., and a solution of 1N HCl (7.75 L) was added slowly over 20 min. After stirring for 10 min, the layers were separated. The organic layer was washed with 5% $NaHCO_3$ (7.75 L), then with 0.5% brine (3 L).

The IPAc solution was filtered via two in-line filters (1 regular, 1 carbon), and the solution was concentrated and azeotropically dried with IPAc (4×4 L). The resultant iPAc solution (~3 L) was crystallized by slow addition of heptane (17 L) at rt. The crystals were allowed to age for 45 min, then filtered. The vessel and crystals were washed with a total of 9:1 heptane:IPAc (15 L). The crystals were dried overnight under vacuum and nitrogen. The mesylate was isolates as a light yellow crystalline solid.

Step 8: Ethyl[(7R)-4-fluoro-7-azido-6,7,8,9-tetrahydropyrido[1,2-α]indol-10-yl]acetate ("azide")

A reaction mixture of the mesylate of Step 7 (1.67 kg, 4.32 mol), DMF (8.35 L), $NaN_3$ (0.457 kg, 7.03 mol) and $Et_3N$ (65 ml, 0.466 mol) under a constant stream of $N_2$ was maintained between 66-70° C. After 18 h, the mixture was cooled to room temperature and $H_2O$ (8.45 L) was slowly added with vigorous stirring. The reaction mixture was filtered; the crystals were washed with 1:1 DMF:$H_2O$ (16 L), 3:7 DMF:$H_2O$ (8.5 L), and water (14 L). The dark brown solid was dried under vacuum and nitrogen.

Recrystallization was carried out by dissolving the brown azide crystals (1.374 kg) under $N_2$ in IPAc (8.25 L). Darco-KB (302 g, 22 wt %) was added and the heterogeneous mixture was stirred for 1.5 h. The resultant suspension was filtered through Solka-Floc, and the filter cake was washed with IPAC (3×4 L) to afford a red solution of the azide in IPAC. The IPAc solution was filtered via in-line filter, concentrated and solvent-switched to heptane. During the addition of heptane, crystallization of azide occurred and heptane was added until a concentration of 94:6 heptane:IPAc (~10 volumes of solvent) was obtained. The reaction vessel was cooled to −20° C. and allowed to age for 1 h. The crystals were filtered cold by pumping and washed with cold (−20° C.) 2:98 IPAc:heptane (8.5 L), followed by 100% heptane (8 L). The azide was isolated as light brown crystals.

Step 9: [3-(4-fluorophenyl)prop-1-yn-1-yl](trimethyl)silane ("TMS alkyne")

N-Methyldicyclohexylamine (2.95 kg, 15.08 mol) was added to a mixture of methanol (10.50 L), tri-t-butylphosphonium tetrafluoroborate (46 g, 0.159 mol) and palladium(II) acetate (18 g, 0.080 mol), and the reaction mixture was degassed for 45 min. 4-Fluorobenzyl bromide (0.980 L, 7.94 mol) and trimethylsilylacetylene (1.225 L, 8.73 mol) were added and the batch was heated to 50° C. for 90 min., then cooled.

At 30° C., heptane (6 L, 4 volumes) was added. At 19.3° C., 1N HCl (6 L, 4 volumes) was added slowly over 22 min to the reaction mixture, which was cooled with an ice-water bath; the temperature was allowed to increase to a maximum of 25.8° C. The biphasic mixture was then transferred by vacuum, via in-line filter into a 50-L jacketed cylindrical vessel. Additional heptane (1.5 L, 1 volume and 0.5 L, ⅓ volume) rinses were also transferred. The mixture was stirred, and the layers allowed to separate. The organic layer was washed with water (6 L, 4 volumes). The dark orange heptane layer was filtered via in-line filter, and heptane was removed by vacuum distillation. The batch was slowly warmed until distillation occurred. Distillation occurred at 112-118° C., suggesting a pressure of ~10 ton (cf.: Gazz. Chim. Ital. 1990, 120, 783: 114° C. at 10 torr).

Step 10:1-fluoro-4-(prop-2-yn-1-yl)benzene ("alkyne")

A solution of the TMS-alkyne of Step 9 (1.48 kg, 5.95 mol) in DMF (1.5 L) was cooled to 6.6° C., and AcOH (0.069 L, 1.205 mol) and additional DMF (total volume of DMF=2.96 L) were added thereto. $Me_4NF \cdot 4H_2O$ (0.250 kg, 1.523 mol) was subsequently introduced in three portions over a period of 15 min. Exotherm was observed after the last batch was introduced, with the temperature increase to 23.1° C. over a period of 5 min before cooling to 5° C. over an additional 15-20 min.

The reaction mixture was cooled back to 0° C. and toluene (3 L) was added, followed by slow addition of 1N HCl (7.5 L, 5 volume). The reaction mixture was stirred and allowed to warm over 30 min to 17° C. The aqueous phase was removed, and the orange organic phase was washed with 1% $NaHCO_3$ (7.5 L) and $H_2O$ (3 L). $Na_2SO_4$ (300 g) was added, and the suspension was allowed to stir for 1 h. After 1 h, the solid was allowed to settle, and the suspension was filtered through an inline filter. The alkyne was stored as a light yellow solution in toluene.

Step 11: Ethyl {(7R)-4-fluoro-7-5-4-fluorobenz 1-1H-[1,2,3]triazol-1-1-6,7,8,9-tetrahydropyrido[1,2-α]indol-10-yl}-acetate ("triazole ester")

Azide of Step 8 (1.125 kg, 3.56 mol) was dissolved in toluene (0.984 L), using a hot plate to offset the endothermic dissolution.

A solution of the alkyne of Step 10, 18.7 wt % in toluene (2.81 kg, 3.91 mol) and Cp*Ru(COD)Cl (0.0236 kg, 0.062 mol) was de-gassed for 30 min., and the reaction mixture was heated to 70° C. The dark red toluene solution of azide was added to the reaction mixture over 50 min. The temperature was maintained at 70° C. for 10 min after the addition, then increased to 90° C. over 15 min. After two hours at 90° C., the internal temperature was increased to 96° C., and the reaction required an additional 7.5 h to complete.

Darco KB-G (400 g, 25 wt %) was added, and the suspension stirred for 90 min. The mixture was filtered through Solka floc, washing with toluene (5×4 L). The combined filtrates were filtered via two in-line filters (1 regular and 1 carbon) and concentrated.

Step 12: {(7R)-4-fluoro-7-5-4-fluorobenz 1-1H-[1,2,3,]triazol-1-1-6,7,8,9-tetrahydropyrido[1,2-α]indol-10-yl}-acetic acid EtOH (2.90 L) was added to the triazole ester of Step 11 (1.45 kg, 3.22 mol), which was obtained as a 22 wt % solution in toluene (4.35 L) under nitrogen, and the mixture was degassed overnight.

Sodium hydroxide (0.773 L, 3.86 mol) was added over 10 min., and the reaction mixture was heated to 50° C. for 2 hours. The reaction mixture was cooled to 33° C. and 1:1 $EtOH:H_2O$ (2.9 L) was added. When the temperature was 25° C., the biphasic mixture was filtered via in-line filter, and the layers were stirred and then separated. The aqueous layer was transferred by vacuum into a clean vessel via 2 in-line filters (1 regular, 1 carbon). Ecosorb C-908 (544 g) was added and the mixture stirred for 75 min. The suspension was filtered through Solka floc, washing with 1:1 $EtOH:H_2O$ (1×3.25 L) and 1:2 $EtOH:H_2O$ (1×3.25 L).

The combined filtrates (16.4 kg) were filtered via 1.0 um in-line filter. The mixture was diluted with THF (2.5 L), added via in-line filter and stirred under nitrogen. Hydrochloric acid (0.308 L, 3.70 mol) was added. The batch was then filtered, and the filter cake was washed with 5:4:2 $H_2O:EtOH:THF$ (1×6 L, 1×5 L), 2:1:1 $H_2O:EtOH:THF$ (1×4 L) and water (1×5 L). The solid was dried under nitrogen and vacuum, and the product was isolated as an off-white crystalline solid.

To the product from the previous step (1.198 kg, 2.84 mol) under nitrogen were added water (3.0 L, 167 mol), EtOH (1.593 L) and THF (2.001 L), followed by sodium hydroxide (0.596 L, 2.98 mol). Darco G-60 (300 g) was charged, and the mixture stirred for 80 min. The mixture was filtered through Solka floc, washing with 5:3:2 $H_2O:THF:EtOH$ (2×2.5 L). The solution was filtered via 1.0 um in-line filter, and hydrochloric acid (0.248 L, 2.98 mol) was added. Crystallization occurred, leading to an extremely thick white suspension; additional 5:3:2 water:THF:EtOH (4.8 L) was added. The batch was filtered, washed with filtered 5:3:2 water:THF: EtOH. The product was isolated as a white crystalline solid containing mostly Form B with some Form C.

To the above crystalline solid (1.095 kg, 2.59 mol) were added THF (4.38 L) and water (4.38 L) via 1.0 uM in-line filter, under nitrogen. The suspension was stirred vigorously for 14 hours. After stirring overnight, the physical properties of the slurry appeared to change from a milky thick suspension that does not settle to a slurry with a yellow supernatant and crystalline solid that settles nicely. The slurry was filtered, and the solid was washed with 3:1 $H_2O:THF$ (4 L, 2 L) and dried under nitrogen and vacuum. After drying for >2 days, the title product Form C was isolated.

X-ray powder diffraction (XRPD) patterns form Form B and Form C are shown in FIGS. 1 and 2, respectively. The XRPD patterns were generated on a Philips Pananalytical X'Pert Pro X-ray powder diffractometer with a PW3040/60 console using a continuous scan from 3 to 40 degrees 2Θ. Copper K-Alpha 1 (Kα1) and K-Alpha 2 (Kα2) radiation was used as the source. The experiment was conducted with the sample at room temperature and open to the atmosphere. 2Θ values and the corresponding d-spacings in the XRPD patterns are included in the tables below.

| Pos.[°2Th] | d-spacing [Å] |
|---|---|
| Form B | |
| 8.3 | 10.7 |
| 8.8 | 10.0 |
| 13.5 | 6.6 |
| 14.0 | 6.3 |

-continued

| Pos.[°2Th] | d-spacing [Å] |
|---|---|
| 15.1 | 5.9 |
| 16.6 | 5.4 |
| 17.8 | 5.0 |
| 18.7 | 4.8 |
| 19.5 | 4.5 |
| 20.2 | 4.4 |
| 21.7 | 4.1 |
| 22.6 | 3.9 |
| 23.2 | 3.8 |
| 24.1 | 3.7 |
| 25.1 | 3.5 |
| 27.8 | 3.2 |
| Form C | |
| 9.5 | 9.3 |
| 11.8 | 7.5 |
| 12.6 | 7.0 |
| 13.7 | 6.5 |
| 16.2 | 5.5 |
| 17.0 | 5.2 |
| 19.1 | 4.7 |
| 19.7 | 4.5 |
| 21.2 | 4.2 |
| 22.4 | 4.0 |
| 23.6 | 3.8 |
| 23.8 | 3.7 |
| 25.3 | 3.5 |
| 25.6 | 3.5 |
| 28.5 | 3.1 |

Differential scanning calorimetry (DSC) curves for Form B and Form C are shown in FIGS. 3 and 4, respectively. These were obtained with a TA Instruments DSC Q 2000 differential scanning calorimeter at a heating rate of 10° C./minute from 25° C. to 265° C. in a closed aluminum pan in a nitrogen atmosphere. The DSC curve of Form B exhibits an endotherm with an onset temperature of 256° C. and a peak temperature of 258° C. The enthalpy change was 108.9 J/g. The endotherm is believed to be due to concomitant melting and decomposition. The DSC curve of Form C exhibits two endotherms. First endotherm shows an onset temperature of 190° C. and a peak temperature of 198° C., with an associated enthalpy change of 22.4 J/g. This endotherm is believed to be due to solid-solid transformation of Form C to Form B. This is followed by a 2nd endotherm with an onset temperature of 257° C. and a peak temperature of 260° C., with an associated enthalpy change of 104.3 J/g. This endotherm was attributed to concomitant melting and decomposition.

EXAMPLE 9

[3-(5-Benzyl-[1,2,3]triazol-1-yl)-1,2,3,4-tetrahydro-carbazol-9-yl]-acetic acid

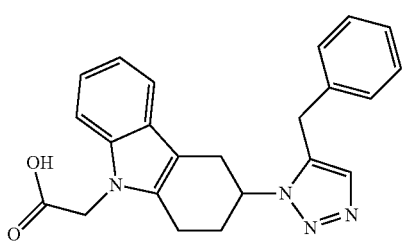 [SMILES: O=C(O)Cn1c2c(c3ccccc31)CC(n1nncc1Cc1ccccc1)CC2]

The title compound was prepared using procedures described in EXAMPLE 7, Step 5 to 8 from ethyl (3-azido-1,2,3,4-tetrahydro-9H-carbazol-9-yl)acetate (*J. Med. Chem.*, 2005, 48, 897) and prop-2-yn-1-ylbenzene. The resulting racemic acid was resolved by HPLC using a 4.6×250 mm Chiralcel OD column eluting with 40% MeOH, 30% iPrOH, 29.75% Hexanes and 0.25% $Et_3N$ at 1 mL/min and 254 nm (retention times=8.9 and 18.3 min) to afford EXAMPLE 9.1 and 9.2 respectively. $^1H$ NMR of EXAMPLE 9.1: $^1H$ NMR (400 MHz, DMSO-$d_6$): δ 12.99 (s, 1 H), 7.53 (s, 1 H), 7.39-7.29 (m, 4 H), 7.31-7.21 (m, 3 H), 7.08 (dd, 1 H), 6.99 (t, 1 H), 4.95-4.84 (m, 2 H), 4.75 (s, 1 H), 4.22 (s, 2 H), 3.20-3.08 (m, 1 H), 3.00 (dd, 1 H), 2.86 (dd, 1 H), 2.79-2.64 (m, 1 H), 2.36-2.27 (m, 1 H), 2.05-1.95 (m, 1 H). MS (+ESI) m/z: 387.1.

EXAMPLE 10

{7-[4-(4-Fluoro-phenyl)-[1,2,3]triazol-1-yl]-6,7,8,9-tetrahydropyrido[1,2-α]indol-10-yl}-acetic acid

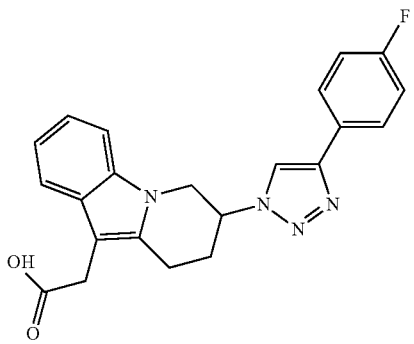 [SMILES: O=C(O)Cc1c2n(c3ccccc13)CC(n1cc(-c3ccc(F)cc3)nn1)CC2]

The title compound was prepared using procedures described in EXAMPLE 1 from propyl (7-azido-6,7,8,9-tetrahydropyrido[1,2-α]indol-10-yl)acetate and 1-ethynyl-4-fluorobenzene. MS (+ESI) m/z: 391.1.

EXAMPLE 11

{7-[4-(4-Methanesulfonylamino-butyl)-[1,2,3]triazol-1-yl]-6,7,8,9-tetrahydropyrido[1,2-α]indol-10-yl}-acetic acid

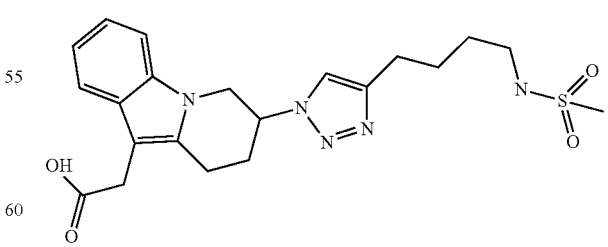

The title compound was prepared using procedures described in EXAMPLE 1 from propyl (7-azido-6,7,8,9-tetrahydropyrido[1,2-α]indol-10-yl)acetate and N-hex-5-yn-1-ylmethanesulfonamide. MS (+ESI) m/z: 446.2.

EXAMPLE 12

{7-[4-(1-Hydroxy-2-methyl-propyl)-[1,2,3]triazol-1-yl]-6,7,8,9-tetrahydropyrido[1,2-α]indol-10-yl}-acetic acid

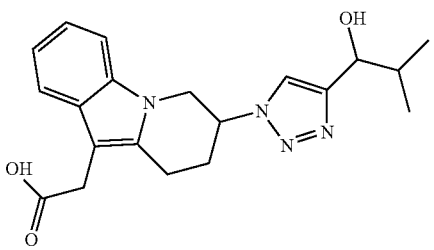 [SMILES: CC(C)C(O)c1cn(C2CCc3c(CC(=O)O)c4ccccc4n3C2)nn1]

The title compound was prepared using procedures described in EXAMPLE 1 from propyl (7-azido-6,7,8,9-tetrahydropyrido[1,2-α]indol-10-yl)acetate and 4-methylpent-1-yn-3-ol. MS (+ESI) m/z: 369.2.

EXAMPLE 13

{7-[4-(1-Hydroxy-1-phenyl-ethyl)-[1,2,3]triazol-1-yl]-6,7,8,9-tetrahydropyrido[1,2-α]indol-10-yl}-acetic acid

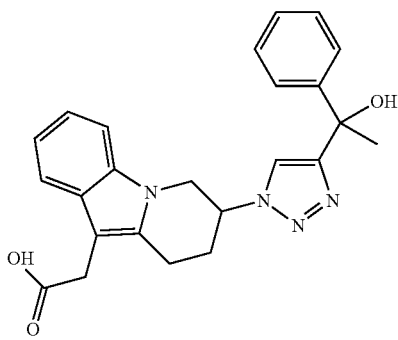 [SMILES: CC(O)(c1ccccc1)c1cn(C2CCc3c(CC(=O)O)c4ccccc4n3C2)nn1]

The title compound was prepared using procedures described in EXAMPLE 1 from propyl (7-azido-6,7,8,9-tetrahydropyrido[1,2-α]indol-10-yl)acetate and 2-phenylbut-3-yn-2-ol. MS (+ESI) m/z: 417.1.

EXAMPLE 14

[7-(4-Phenoxymethyl-[1,2,3]triazol-1-yl)-6,7,8,9-tetrahydropyrido[1,2-α]indol-10-yl]-acetic acid

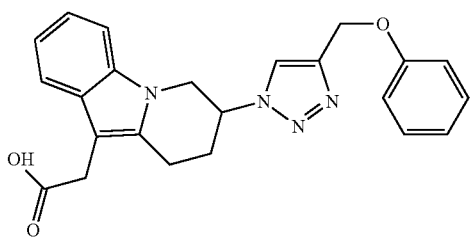 [SMILES: O=C(O)Cc1c2n(c3ccccc13)CC(n1cc(COc3ccccc3)nn1)CC2]

The title compound was prepared using procedures described in EXAMPLE 1 from propyl (7-azido-6,7,8,9-tetrahydropyrido[1,2-α]indol-10-yl)acetate and phenyl prop-2-yn-1-yl ether. MS (+ESI) m/z: 403.2.

EXAMPLE 15

{7-[4-(4-Methanesulfonyl-phenyl)-[1,2,3]triazol-1-yl]-6,7,8,9-tetrahydropyrido[1,2-α]indol-10-yl}-acetic acid

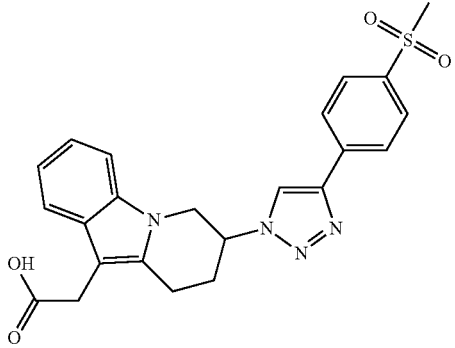 [SMILES: CS(=O)(=O)c1ccc(-c2cn(C3CCc4c(CC(=O)O)c5ccccc5n4C3)nn2)cc1]

The title compound was prepared using procedures described in EXAMPLE 1 from propyl (7-azido-6,7,8,9-tetrahydropyrido[1,2-α]indol-10-yl)acetate and 1-ethynyl-4-(methylsulfonyl)benzene. MS (+ESI) m/z: 451.1.

EXAMPLE 16

(7-{4-[4-(1-Hydroxy-1-methyl-ethyl)-phenyl]-[1,2,3]triazol-1-yl}-6,7,8,9-tetrahydropyrido[1,2-α]indol-10-yl)-acetic acid

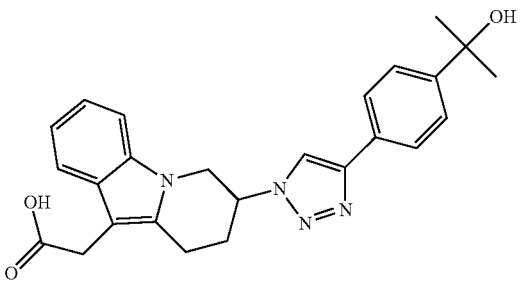 [SMILES: CC(C)(O)c1ccc(-c2cn(C3CCc4c(CC(=O)O)c5ccccc5n4C3)nn2)cc1]

The title compound was prepared using procedures described in EXAMPLE 1 from propyl (7-azido-6,7,8,9-tetrahydropyrido[1,2-α]indol-10-yl)acetate and 2-(4-ethynylphenyl)propan-2-ol. MS (+ESI) m/z: 431.2.

EXAMPLE 17

{7-[4-(4-Trifluoromethyl-phenyl)-[1,2,3]triazol-1-yl]-6,7,8,9-tetrahydropyrido[1,2-α]indol-10-yl}acetic acid

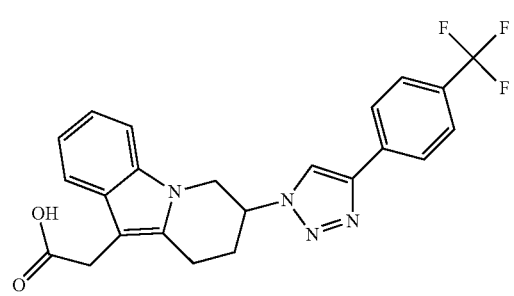 [SMILES: O=C(O)Cc1c2n(c3ccccc13)CC(n1cc(-c3ccc(C(F)(F)F)cc3)nn1)CC2]

The title compound was prepared using procedures described in EXAMPLE 1 from propyl (7-azido-6,7,8,9-tetrahydropyrido[1,2-α]indol-10-yl)acetate and 1-ethynyl-4-(trifluoromethyl)benzene. MS (+ESI) m/z: 441.1.

EXAMPLE 18

[7-(4-Naphthalen-1-yl-[1,2,3]triazol-1-yl)-6,7,8,9-tetrahydropyrido[1,2-α]indol-10-yl]-acetic acid

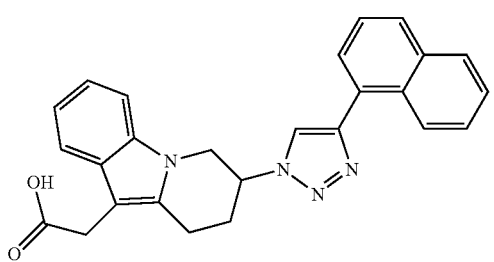 [SMILES: O=C(O)Cc1c2n(c3ccccc13)CC(n1cc(-c3cccc4ccccc34)nn1)CC2]

The title compound was prepared using procedures described in EXAMPLE 1 from propyl (7-azido-6,7,8,9-tetrahydropyrido[1,2-α]indol-10-yl)acetate and 1-ethynyl-naphthalene. MS (+ESI) m/z: 423.2.

EXAMPLE 19

{7-[4-(4-Dimethylamino-phenyl)-[1,2,3]triazol-1-yl]-6,7,8,9-tetrahydropyrido[1,2-α]indol-10-yl}-acetic acid

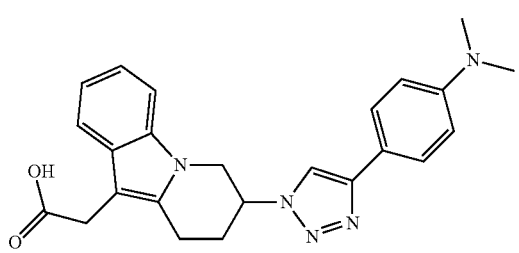 [SMILES: CN(C)c1ccc(-c2cn(C3CCc4c(CC(=O)O)c5ccccc5n4C3)nn2)cc1]

The title compound was prepared using procedures described in EXAMPLE 1 from propyl (7-azido-6,7,8,9-tetrahydropyrido[1,2-α]indol-10-yl)acetate and 4-ethynyl-N,N-dimethylaniline. MS (+ESI) m/z: 416.2.

EXAMPLE 20

{7-[5-(4-Fluoro-phenyl)-[1,2,3]triazol-1-yl]-6,7,8,9-tetrahydropyrido[1,2-α]indol-10-yl}-acetic acid

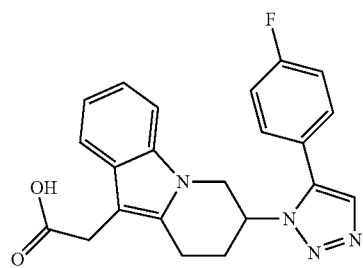 [SMILES: O=C(O)Cc1c2n(c3ccccc13)CC(n1nncc1-c1ccc(F)cc1)CC2]

The title compound was prepared using procedures described in EXAMPLE 3 from propyl (7-azido-6,7,8,9-tetrahydropyrido[1,2-α]indol-10-yl)acetate and 1-ethynyl-4-fluorobenzene. MS (+ESI) m/z: 391.1.

EXAMPLE 21

[7-(5-Phenoxymethyl-[1,2,3]triazol-1-yl)-6,7,8,9-tetrahydropyrido[1,2-α]indol-10-yl]-acetic acid

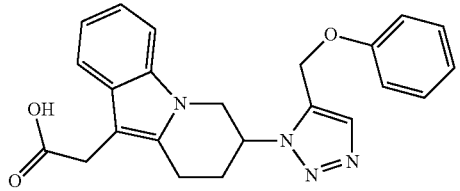 [SMILES: O=C(O)Cc1c2n(c3ccccc13)CC(n1nncc1COc1ccccc1)CC2]

The title compound was prepared using procedures described in EXAMPLE 3 from propyl (7-azido-6,7,8,9-tetrahydropyrido[1,2-α]indol-10-yl)acetate and (prop-2-yn-1-yloxy)benzene. MS (+ESI) m/z: 403.1.

EXAMPLE 22

(7-{5-[(4-Bromo-phenyl)-hydroxy-methyl]-[1,2,3]triazol-1-yl}-6,7,8,9-tetrahydropyrido[1,2-α]indol-10-yl)-acetic acid

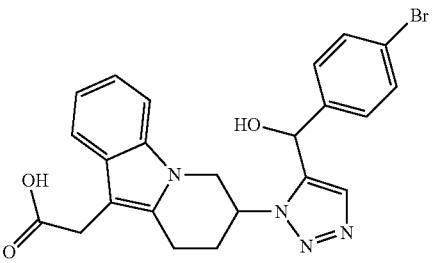 [SMILES: O=C(O)Cc1c2n(c3ccccc13)CC(n1nncc1C(O)c1ccc(Br)cc1)CC2]

The title compound was prepared using procedures described in EXAMPLE 3 from propyl (7-azido-6,7,8,9-tetrahydropyrido[1,2-α]indol-10-yl)acetate and 1-(4-bromophenyl)prop-2-yn-1-ol. MS (+ESI) m/z: 483.0.

EXAMPLE 23

4-[3-(10-Carboxymethyl-6,7,8,9-tetrahydropyrido[1,2-α]indol-7-yl)-3H-[1,2,3]triazol-4-yl]-piperidine-1-carboxylic acid tert-butyl ester

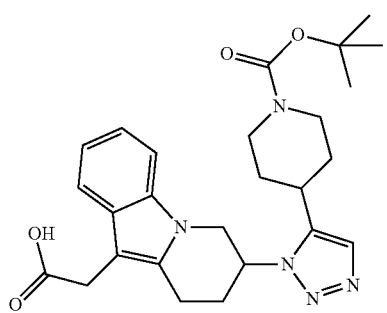 [SMILES: CC(C)(C)OC(=O)N1CCC(c2cnnn2C2CCc3c(CC(=O)O)c4ccccc4n3C2)CC1]

The title compound was prepared using procedures described in EXAMPLE 3 from propyl (7-azido-6,7,8,9-tetrahydropyrido[1,2-α]indol-10-yl)acetate and tert-butyl 4-ethynylpiperidine-1-carboxylate. MS (+ESI) m/z: 480.2.

EXAMPLE 24

[7-(5-Cyclohexyl-[1,2,3]triazol-1-yl)-6,7,8,9-tetrahydropyrido[1,2-α]indol-10-yl]-acetic acid

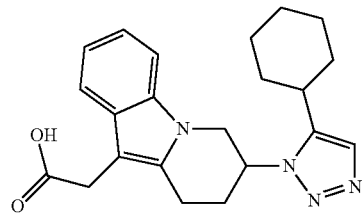 [SMILES: O=C(O)Cc1c2n(c3ccccc13)CC(n1nncc1C1CCCCC1)CC2]

The title compound was prepared using procedures described in EXAMPLE 3 from propyl (7-azido-6,7,8,9-tetrahydropyrido[1,2-α]indol-10-yl)acetate and ethynylcyclohexane. MS (+ESI) m/z: 379.2.

EXAMPLE 25

{7-[5-(9-Hydroxy-9H-fluoren-9-yl)-[1,2,3]triazol-1-yl]-6,7,8,9-tetrahydropyrido[1,2-α]indol-10-yl}-acetic acid

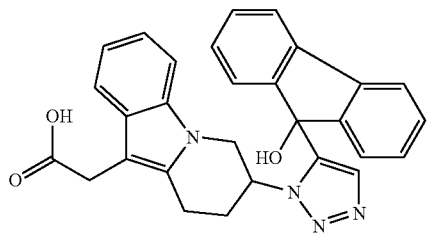 [SMILES: O=C(O)Cc1c2n(c3ccccc13)CC(n1nncc1C1(O)c3ccccc3-c3ccccc31)CC2]

The title compound was prepared using procedures described in EXAMPLE 3 from propyl (7-azido-6,7,8,9-tetrahydropyrido[1,2-α]indol-10-yl)acetate and 9-ethynyl-9H-fluoren-9-ol. MS (+ESI) m/z: 477.1.

EXAMPLE 26

(7-{5-[1-(4-Fluoro-phenyl)-vinyl]-[1,2,3]triazol-1-yl}-6,7,8,9-tetrahydropyrido[1,2-α]indol-10-yl)-acetic acid

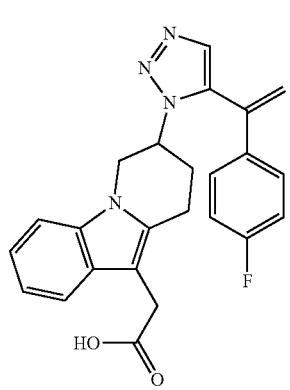 [SMILES: C=C(c1ccc(F)cc1)c1cnnn1C1CCc2c(CC(=O)O)c3ccccc3n2C1]

The title compound was prepared from refluxing a solution of (7-{5-[1-(4-Fluoro-phenyl)-1-hydroxy-ethyl]-[1,2,3]triazol-1-yl}-6,7,8,9-tetrahydropyrido[1,2-α]indol-10-yl)-acetic acid (EXAMPLE 5) in a 1:1 mixture of Dioxane: 2M HCl for 24 h. The reaction mixture was cooled to room temperature then extracted with EA, washed with brine, dried over Na$_2$SO$_4$ and evaporated. Purification by Combi-flash EA/Hex 50-100% afforded the desired compound. MS (+ESI) m/z: 417.1.

EXAMPLE 27

(7-{(R)-5-[Bis-(4-fluoro-phenyl)-hydroxy-methyl]-[1,2,3]triazol-1-yl}-6,7,8,9-tetrahydro-pyrido[1,2-α]indol-10-yl)-acetic acid

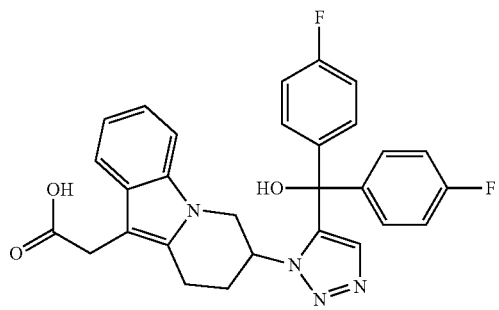 [SMILES: O=C(O)Cc1c2n(c3ccccc13)CC(n1nncc1C(O)(c1ccc(F)cc1)c1ccc(F)cc1)CC2]

The title compound was prepared from enantiomerically pure propyl (7-azido-6,7,8,9-tetrahydropyrido[1,2-α]indol-10-yl)acetate described in EXAMPLE 6 and 1,1-bis(4-fluorophenyl)prop-2-yn-1-ol. EXAMPLE 27.1 and 27.2 were prepared from the chiral azide with the retention time of 10.3 and 11.5 min respectively from EXAMPLE 6. MS (+ESI) m/z: 515.2.

EXAMPLE 28

{(R)-7-[5-(4-Fluoro-benzyl)-[1,2,3]triazol-1-yl]-6,7,8,9-tetrahydropyrido[1,2-α]indol-10-yl}-acetic acid

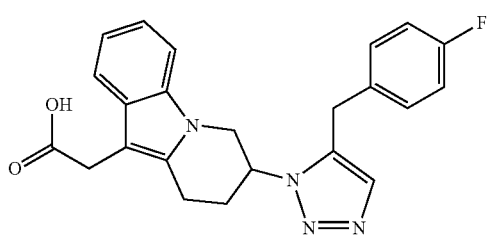 [SMILES: O=C(O)Cc1c2n(c3ccccc13)CC(n1nncc1Cc1ccc(F)cc1)CC2]

The title compound was prepared using enantiomerically pure propyl (7-azido-6,7,8,9-tetrahydropyrido[1,2-α]indol-10-yl)acetate from EXAMPLE 6 and 1-fluoro-4-prop-2-yn-1-ylbenzene prepared from 4-fluorobenzyl chloride and ethynyltrimethylsilane described in EXAMPLE 8 EXAMPLE 28.1 and 28.2 were prepared from the chiral azide with the retention time of 10.3 and 11.5 min respectively from EXAMPLE 6. MS (+ESI) m/z: 405.1.

EXAMPLE 29

{(R)-7-[5-(1-Phenyl-ethyl)-[1,2,3]triazol-1-yl]-6,7,8,9-tetrahydropyrido[1,2-α]indol-10-yl}-acetic acid

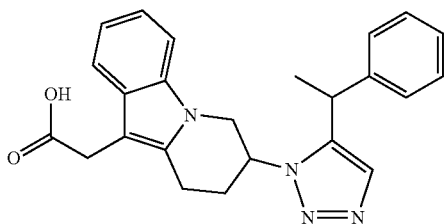 [SMILES: CC(c1ccccc1)c1cnnn1C1CCc2c(CC(=O)O)c3ccccc3n2C1]

The title compound was prepared using procedures described in EXAMPLE 8 from both enantiomerically pure propyl (7-azido-6,7,8,9-tetrahydropyrido[1,2-α]indol-10-yl) acetate and (1-methylprop-2-yn-1-yl)benzene prepared from (1-bromoethyl)benzene and ethynyltrimethylsilane. The resulting diastereoisomeric esters derived from the chiral azide with the retention time of 10.3 min from EXAMPLE 6 were separated by flash chromatography using a gradient of 10-70% EA/Hex to afford after standard hydrolysis EXAMPLE 29.1 and 29.2. The resulting diastereoisomeric esters derived from the chiral azide with the retention time of 11.5 min from EXAMPLE 6 were separated by flash chromatography using a gradient of 10-70% EA/Hex to afford after standard hydrolysis EXAMPLE 29.3 and 29.4 respectively. MS (+ESI) m/z: 405.1.

EXAMPLE 30

((R)-7-{5-[Bis-(4-fluoro-phenyl)-methyl]-[1,2,3]triazol-1-yl}-6,7,8,9-tetrahydropyrido[1,2-α]indol-10-yl)-acetic acid

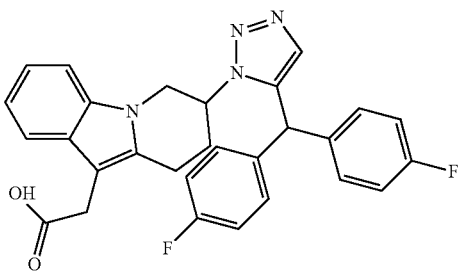 [SMILES: O=C(O)Cc1c2n(c3ccccc13)CC(n1nncc1C(c1ccc(F)cc1)c1ccc(F)cc1)CC2]

The title compound was prepared using procedures described in EXAMPLE 8 from enantiomerically pure propyl (7-azido-6,7,8,9-tetrahydropyrido[1,2-α]indol-10-yl)acetate and 1,1'-prop-1-yne-3,3-diylbis(4-fluorobenzene) MS (+ESI) m/z: 499.2.

EXAMPLE 31

((R)-7-{5-[1-(4-fluorophenyl)-1-hydroxyethyl]-[1,2,3]triazol-1-yl}-6,7,8,9-tetrahydropyrido[1,2-α]indol-10-yl)-acetic acid

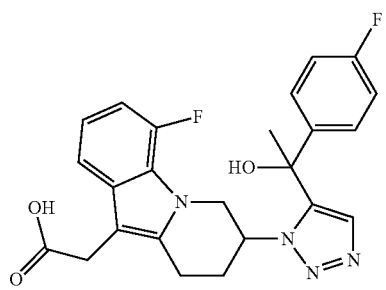 [SMILES: CC(O)(c1ccc(F)cc1)c1cnnn1C1CCc2c(CC(=O)O)c3cccc(F)c3n2C1]

The title compound was prepared using procedures described in EXAMPLE 8 from propyl (7-azido-4-fluoro-6,7,8,9-tetrahydropyrido[1,2-α]indol-10-yl)acetate and 2-(4-fluorophenyl)but-3-yn-2-ol. Separation of the resulting diastereoisomers was performed at the ester stage by flash chromatography using a gradient of 10-100% EA/Hex afforded 2 esters. The faster eluting enantiomeric mixture was resolved on chiral HPLC using a 4.6×250 mm Chiralcel OD column eluting with 20% iPrOH, 20% EtOH, 59.75% Hexanes and 0.25% Et₃N at 1 mL/min and 254 nm. Retention times=6.9 and 8.4 min. The 2 resulting esters were hydrolyzed separately to afford EXAMPLE 31.1 and 31.2 respectively. The slower eluting enantiomeric mixture was resolved on chiral HPLC using a 4.6×250 mm Chiralcel OD eluting with 20% iPrOH, 20% EtOH, 60% Hexanes at 1 mL/min and 254 nm. Retention times=8.7 and 11.6 min. The 2 resulting esters were hydrolyzed separately to afford EXAMPLE 31.3 and 31.4 respectively. MS (+ESI) m/z: 453.1.

EXAMPLE 32

{4-Fluoro-7-[5-(1-phenyl-ethyl)-[1,2,3]triazol-1-yl]-6,7,8,9-tetrahydropyrido[1,2-α]indol-10-yl}-acetic acid

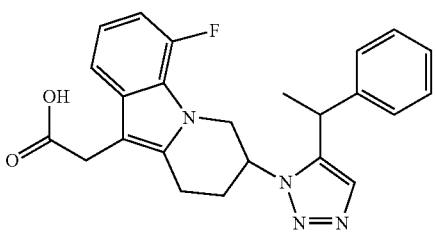 [SMILES: CC(c1ccccc1)c1cnnn1C1CCc2c(CC(=O)O)c3cccc(F)c3n2C1]

The title compound was prepared using procedures described in EXAMPLE 8 from propyl (7-azido-4-fluoro-6,7,8,9-tetrahydropyrido[1,2-α]indol-10-yl)acetate and (1-methylprop-2-yn-1-yl)benzene prepared from (1-bromoethyl)benzene and ethynyltrimethylsilane. Separation of the resulting diastereoisomeric esters by flash chromatography using a gradient of 10-70% EA/Hex afforded 2 enantiomeric mixtures. The less polar enantiomeric mixture was resolved on chiral HPLC using a 4.6×250 mm Chiralpak AD column eluting with 20% iPrOH, 20% EtOH, 59.75% Hexanes and 0.25% Et₃N at 1 mL/min and 254 nm. The resulting chiral esters (retention times=7.8 and 11.9 min) were hydrolyzed separately to afford EXAMPLE 32.1 and 32.2 respectively. The more polar enantiomeric mixture was resolved on chiral HPLC using a 4.6×250 mm Chiralcel OD column eluting with 20% MeOH, 20% EtOH, 60% Hexanes at 1 mL/min and 254 nm. The resulting chiral esters (retention times=9.6 and 10.5 min) were hydrolyzed separately to afford EXAMPLE 32.3 and 32.4 respectively. MS (+ESI) m/z: 419.2.

The following compounds were prepared using analogous procedures described in EXAMPLE 8.

| EX | STRUCTURE | IUPAC | ION OBS'D |
|---|---|---|---|
| 33 | 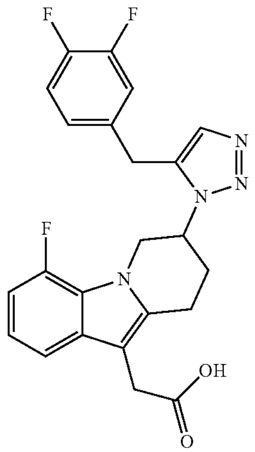 [SMILES: O=C(O)Cc1c2n(c3c(F)cccc13)CC(n1nncc1Cc1ccc(F)c(F)c1)CC2] | {7-[5-(3,4-difluorobenzyl)-1H-1,2,3-triazol-1-yl]-4-fluoro-6,7,8,9-tetrahydropyrido[1,2-a]-indol-10-yl}acetic acid resolved as Examples 33.1 and 33.2 | 441 |
| 34 | 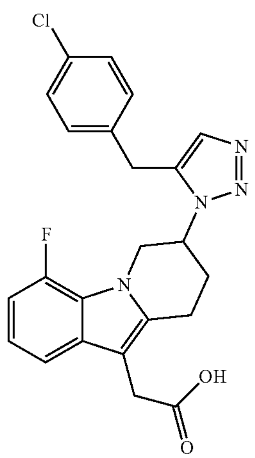 [SMILES: O=C(O)Cc1c2n(c3c(F)cccc13)CC(n1nncc1Cc1ccc(Cl)cc1)CC2] | {7-[5-(4-chlorobenzyl)-1H-1,2,3-triazol-1-yl]-4-fluoro-6,7,8,9-tetrahydropyrido[1,2-a]indol-10-yl}acetic acid resolved as Examples 34.1 and 34.2 | 440 |
| 35 | 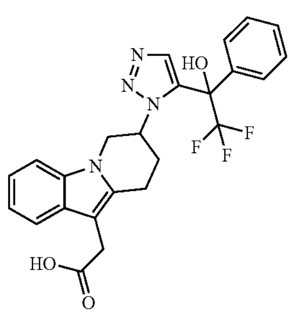 [SMILES: O=C(O)Cc1c2n(c3ccccc13)CC(n1nncc1C(O)(c1ccccc1)C(F)(F)F)CC2] | {7-[5-(2,2,2-trifluoro-1-hydroxy-1-phenyl-ethyl)-1H-1,2,3-triazol-1-yl]-6,7,8,9-tetrahydropyrido[1,2-a]indol-10-yl}acetic acid | 471 |

EXAMPLE 36

{4-Fluoro-7-[5-(4-fluorobenzyl)-4-methyl-1H-1,2,3-triazol-1-yl]-6,7,8,9-tetrahydropyrido[1,2-a]indol-10-yl}acetic acid

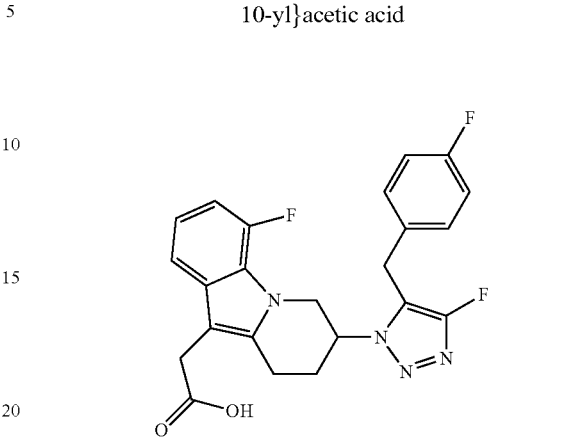

Step 1: 1-(But-2-yn-1-yl)-4-fluorobenzene

A solution of 1-fluoro-4-(prop-2-yn-1-yl)benzene in THF (0.3 M) was treated at 0° C. with a 2.5 M solution of n-BuLi in hexanes (1.2 eq.), stirred 10 min, followed by addition of MeI (1.4 eq.). Removed cooling bath, and allowed reaction mixture to stir for 30 min. Quenched with saturated $NH_4Cl$, diluted with ether, washed with water, dried ($Na_2SO_4$), and concentrated to provide the desired methyl-substituted alkyne intermediate 1-(but-2-yn-1-yl)-4-fluorobenzene: $^1$H NMR (600 MHz, $CDCl_3$) δ 7.24-7.28 (m, 2 H), 6.96-6.98 (m, 2 H), 3.49 (s, 2 H), 1.83 (s, 3 H).

Step 2: Ethyl {4-fluoro-7-[5-(4-fluorobenzyl)-4-methyl-1H-1,2,3-triazol-1-yl]-6,7,8,9-tetrahydropyrido[1,2-α]indol-10-yl}acetate and ethyl{4-fluoro-7-[4-(4-fluorobenzyl)-5-methyl-1H-1,2,3-triazol-1-yl]-6,7,8,9-tetrahydropyrido[1,2-α]indol-10-yl}acetate.

A solution of racemic ethyl (7-azido-4-fluoro-6,7,8,9-tetrahydropyrido[1,2-a]indol-10-yl)acetate and 1-(but-2-yn-1-yl)-4-fluorobenzene (5 eq.) in benzene (0.3 M) was treated with ClCp*(COD)Ru(II) (0.25 eq.). The mixture was warmed to 80° C., stirred overnight, and concentrated to an oil. Chromatography on $SiO_2$ (0-50% EtOAc/DCM) gave the intermediate triazolyl ester as an inseparable 4:1 mixture of regioisomers favoring the 4-methyl-1,2,3-triazole substitution. First the two regioisomers were separated using achiral reverse phase chromatography. The major regioisomer was then further purified using chiral supercritical fluid column chromatography (Chiral Technology AS-H 2.1×25 cm column, 30% IPA/$CO_2$) to provide two chiral esters. MS (EI) calc'd for C26H27F2N4O2 [M+1]+465.2, found 465.1.

Step 3: {4-Fluoro-7-[5-(4-fluorobenzyl)-4-methyl-1H-1,2,3-triazol-1-yl]-6,7,8,9-tetrahydropyrido[1,2-α]indol-10-yl}acetic acid Each of the chiral resolved ethyl {4-fluoro-7-[5-(4-fluorobenzyl)-4-methyl-1H-1,2,3-triazol-1-yl]-6,7,8,9-tetrahydropyrido[1,2-α]indol-10-yl}acetate was hydrolyzed to the final acid product by dissolving in 1:1:1 THF/MeOH/water (0.06 M), treating with LiOH (3.6 eq.) and stirring overnight. The reaction mixture was diluted with EtOAc, extracted with 2 N HCl, water, dried (Na$_2$SO$_4$), and concentrated to provide {4-fluoro-7-[5-(4-fluorobenzyl)-4-methyl-1H-1,2,3-triazol-1-yl]-6,7,8,9-tetrahydropyrido[1,2-α]indol-10-yl}acetic acid Examples 36.1 and 36.2: MS (EI) calc'd for C24H23F2N4O2 [M+1]+437.2, found 437.1.

EXAMPLE 37

{4-Fluoro-7-[4-(4-fluorobenzyl)-5-methyl-1H-1,2,3-triazol-1-yl]-6,7,8,9-tetrahydropyrido[1,2-α]indol-10-yl}acetic acid

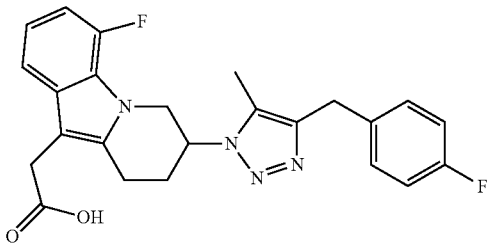 [SMILES: Cc1c(Cc2ccc(F)cc2)nnn1C1CCc2c(CC(=O)O)c3cccc(F)c3n2C1]

The racemic ethyl {4-fluoro-7-[4-(4-fluorobenzyl)-5-methyl-1H-1,2,3-triazol-1-yl]-6,7,8,9-tetrahydropyrido[1,2-α]indol-10-yl}acetate (as described in Example 36) was hydrolyzed to the final acid product by dissolving in 1:1:1 THF/MeOH/water (0.06 M), treating with LiOH (3.6 eq.) and stirring overnight. The reaction mixture was then diluted with EtOAc, extracted with 2 N HCl, water, dried (Na$_2$SO$_4$), and concentrated to provide the title compound: MS (EI) calc'd for C24H23F2N4O2 [M+1]+437.2, found 437.1.

EXAMPLE 38

{4-Fluoro-7-[5-(4-fluorobenzyl)-1H-1,2,3-triazol-1-yl]-6-methyl-6,7,8,9-tetrahydropyrido[1,2-α]indol-10-yl}acetic acid

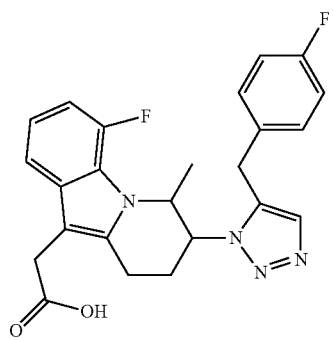 [SMILES: CC1C(n2nncc2Cc2ccc(F)cc2)CCc2c(CC(=O)O)c3cccc(F)c3n21]

Step 1: Propyl (4-Fluoro-6-methyl-7-oxo-6,7,8,9-tetrahydropyrido[1,2-α]indol-10-yl)acetate A solution of propyl (4-fluoro-7-oxo-6,7,8,9-tetrahydropyrido[1,2-α]indol-10-yl)acetate in THF (0.17 M) was treated at −78° C. with a 1.0 M solution of NaHMDS in THF (1.2 eq.). After stirring for 10 min, MeI (2.0 eq.) was added. The cooling bath was removed and the mixture stirred for 1 hour, concentrated to dryness and the residue purified by chromatography on SiO$_2$ (0-100% EtOAc/hexanes).

Step 2: Propyl (4-Fluoro-7-hydroxy-6-methyl-6,7,8,9-tetrahydropyrido[1,2-a]indol-10-yl)acetate A solution of the intermediate methyl ketone from step 1 in THF (0.25 M) was treated with NaBH$_4$ (2.0 eq.) and stirred for 1 hour, diluted with DCM, extracted with water, dried (Na$_2$SO$_4$) and concentrated giving the intermediate alcohol. MS (EI) calc'd for C18H23FNO3 [M+1]+320.2, found 320.1.

Step 3: Propyl {4-Fluoro-6-methyl-7-[(methylsulfonyl)oxy]-6,7,8,9-tetrahydropyrido [1,2-α]indol-10-yl}acetate A solution of the intermediate alcohol from step 2 (80 mg, 0.25 mmol) in 2 mL of DCM (1 M) was treated at 0° C. with Hunig's base (2 eq.) and MsCl (1.5 eq.). After stirring for 30 min, the mixture was diluted with DCM, extracted with 1 M citric acid, water, dried (Na$_2$SO$_4$) and concentrated.

Step 4: Propyl (7-Azido-4-fluoro-6-methyl-6,7,8,9-tetrahydropyrido[1,2-α]indol-10-yl)acetate Propyl {4-fluoro-6-methyl-7-[(methylsulfonyl)oxy]-6,7,8,9-tetrahydropyrido[1,2-α]indol-10-yl}acetate was dissolved in DMF (1 M) and treated with NaN$_3$ (2.0 eq.), warmed to 80° C. and stirred overnight. The reaction mixture was diluted with EtOAc and extracted with sat'd NH$_4$Cl, water, dried (Na2SO4) and concentrated. Chromatography on SiO2 (0-100% EtOAc/hexanes) gave propyl (7-azido-4-fluoro-6-methyl-6,7,8,9-tetrahydropyrido[1,2-α]indol-10-yl)acetate: $^1$H NMR (600 MHz, CDCl$_3$) δ 7.30 (d, J=7.9 Hz, 1 H), 6.96-6.99 (m, 1 H), 6.80 (dd, J=12.6, 7.6 Hz, 1 H), 4.87 (dd, J=13.2, 6.5 Hz, 1 H), 4.10 (d, J=7.0 Hz, 1 H), 4.02 (t, J=6.2 Hz, 2 H), 3.61 (m, 2 H), 3.01 (m, 2 H), 2.10-2.20 (m, 2 H), 1.57-1.63 (m, 2 H), 1.43 (d, J=6.8 Hz, 3 H), 0.87 (t, J=7.3 Hz, 3 H); MS (EI) calc'd for C18H22FN4O2 [M+1]+345.2, found 345.1.

Step 5: Propyl {4-Fluoro-7-[5-(4-fluorobenzyl)-1H-1,2,3-triazol-1-yl]-6-methyl-6,7,8,9-tetrahydropyrido[1,2-a]indol-10-yl}acetate A solution of racemic propyl (7-azido-4-fluoro-6-methyl-6,7,8,9-tetrahydropyrido[1,2-α]indol-10-yl)acetate and 1-fluoro-4-(prop-2-yn-1-yl)benzene (5 eq.) in benzene (0.1 M) was treated with ClCp*(COD)Ru(II) (0.4 eq.). The mixture was warmed to 80° C., stirred overnight and concentrated to an oil. Chromatography on SiO$_2$ (0-50% EtOAc/DCM) gave the intermediate triazolyl ester. The enantiomers were resolved using chiral supercritical fluid chromatography using SFC (Chiral Technology AS-H 2.1×25 cm column, 30% IPA/CO$_2$): MS (EI) calc'd for C$_{27}$H$_{29}$F$_2$N$_{4}$O$_2$ [M+1]+ 479.2, found 479.1.

Step 6: {4-Fluoro-7-[5-(4-fluorobenzyl)-1H-1,2,3-triazol-1-yl]-6-methyl-6,7,8,9-tetrahydropyrido[1,2-α]indol-10-yl}acetic Acid The two resolved chiral ethyl esters were each hydrolyzed to the corresponding acid product by dissolving in 1:1:1 THF/MeOH/water (0.01 M), treating with LiOH (10 eq.) and stirring for 1 hour. The mixture was diluted with EtOAc, extracted with 2 N HCl, water, dried (Na$_2$SO$_4$), and concentrated to provide {4-fluoro-7-[5-(4-fluorobenzyl)-1H-1,2,3-triazol-1-yl]-6-methyl-6,7,8,9-tetrahydropyrido[1,2-a]indol-10-yl}acetic acid as Example 38.1 and 38.2: MS (EI) calc'd for C24H23F2N4O2 [M+1]+437.2, found 437.1.

EXAMPLE 39

(4-Fluoro-7-{5-[1-(4-fluorophenyl)-1-methylethyl]-1H-1,2,3-triazol-1-yl}-6,7,8,9-tetrahydropyrido[1,2-a]indol-10-yl)acetic acid

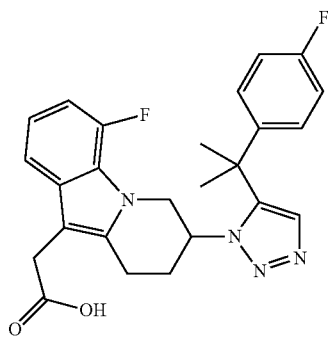 [SMILES: CC(C)(c1ccc(F)cc1)c1cnnn1C1CCc2c(CC(=O)O)c3cccc(F)c3n2C1]

Step 1: Methyl 2-(4-Fluorophenyl)-2-methylpropanoate

A solution of methyl (4-fluorophenyl)acetate in THF (1.8 M) was treated at 0° C. with 60% NaH in mineral oil (1.1 eq.), stirred 20 min, then treated with MeI (1.3 eq.). After stirring for 5 hours, the reaction mixture was charged with additional 60% NaH (1.1 eq.) and MeI (1.3 eq.). The reaction was then stirred overnight, diluted with DCM and extracted with water, dried ($Na_2SO_4$), and concentrated.

Step 2: 2-(4-Fluorophenyl)-2-methylpropan-1-ol

The ester from step 1 was reduced by dissolving in THF (0.15 M) and treating with LiBH4 (5 eq.) and stirring for 15 hours. The reaction mixture was quenched with water and extracted with DCM, the organic layer dried ($Na_2SO_4$) and concentrated to provide oily 2-(4-fluorophenyl)-2-methylpropan-1-ol: $^1$H NMR (600 MHz, CDCl$_3$) δ 7.31-7.34 (m, 2 H), 6.99-7.02 (m, 2 H), 3.58 (d, J=5.8 Hz, 2 H), 1.30 (s, 6 H).

Step 3: 2-(4-Fluorophenyl)-2-methylpropanal

A solution of DMSO (1.7 eq.) in DCM (0.5 M) was treated at −78° C. with a 2 M solution of oxalyl chloride in DCM (1.4 eq.). The reaction was stirred for 5 min, and a solution of 2-(4-fluorophenyl)-2-methylpropan-1-ol (1 eq.) in DCM (3 M) added to the reaction mixture. After stirring for 10 min, NEt$_3$ (2.4 eq.) was added and the reaction mixture warmed to 0° C., stirred one hour, removed the cooling bath and stirred for one additional hour. The mixture was diluted with DCM, extracted with bleach/water, 1 M citric acid, water, dried ($Na_2SO_4$), concentrated.

Step 4: 1-Fluoro-4-(2-methylbut-3-yn-2-yl)benzene

Next, a solution of dimethyl (1-diazo-2-oxopropyl)phosphonate (1.4 eq.) in MeOH (0.6 M) was treated at 0° C. with K2CO3 (2.4 eq.) and 2-(4-fluorophenyl)-2-methylpropanal (1.0 eq.). The reaction mixture was stirred for 1 hour, diluted with EtOAc, washed with water, dried ($Na_2SO_4$) and concentrated giving 1-fluoro-4-(2-methylbut-3-yn-2-yl)benzene: 1H NMR (600 MHz, CDCl$_3$) δ 7.48-7.50 (m, 2 H), 6.97-7.00 (m, 2 H), 2.33 (s, 1 H), 1.57 (s, 6 H).

Step 5: Ethyl (4-Fluoro-7-{5-[2-(4-fluorophenyl)propan-2-yl]-1H-1,2,3-triazol-1-yl}-6,7,8,9-tetrahydropyrido[1,2-α]indol-10-yl)acetate A solution of racemic ethyl (7-azido-4-fluoro-6,7,8,9-tetrahydropyrido[1,2-a]-indol-10-yl)acetate and 1-fluoro-4-(2-methylbut-3-yn-2-yl)benzene (3 eq.) in benzene (0.2 M) was treated with ClCp*(COD)Ru(II) (0.2 eq.). The mixture was warmed to 80° C., stirred overnight, and concentrated to an oil. Chromatography on SiO$_2$ (0-50% EtOAc/DCM) gave the intermediate triazolyl ester: MS (EI) calc'd for C27H29F2N4O2 [M+1]+479.2, found 479.2.

Step 6: (4-Fluoro-7-{5-[1-(4-fluorophenyl)-1-methylethyl]-1H-1,2,3-triazol-1-yl}-6,7,8,9-tetrahydropyrido[1,2-α]indol-10-yl)acetic Acid The ethyl ester was hydrolyzed to the racemic acid product by dissolving in 1:1:1 THF/MeOH/water (0.07 M), treating with LiOH (4 eq.) and stirring overnight. The mixture was diluted with EtOAc, extracted with 2 N HCl, water, dried (Na2SO4), and concentrated. The residue was resolved using chiral supercritical fluid chromatography (Chiral Technology AS-H 2.1×25 cm column, 0.25% TFA/40% IPA/CO$_2$) to provide the title compound: MS (EI) calc'd for C25H25F2N4O2 [M+1]+451.2, found 451.1.

The following compounds were prepared using analogous procedures described in EXAMPLE 8.

| EX | STRUCTURE | IUPAC | ION OBS'D |
|---|---|---|---|
| 40 | 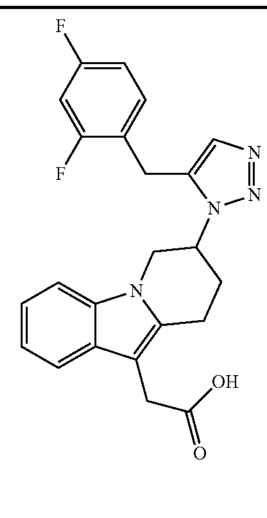 | Chiral {7-[5-(2,4-difluorobenzyl)-1H-1,2,3-triazol-1-yl]-6,7,8,9-tetrahydropyrido[1,2-a]-indol-10-yl}acetic acid | 423 |

-continued

| EX | STRUCTURE | IUPAC | ION OBS'D |
|---|---|---|---|
| 41 | 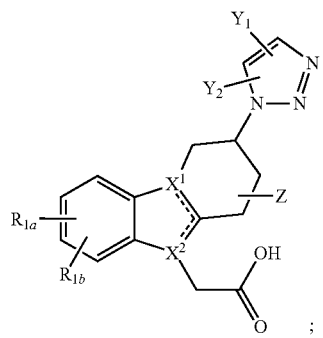 | Chiral {7-[5-(2,4-difluorobenzyl)-1H-1,2,3-triazol-1-yl]-4-fluoro-6,7,8,9-tetrahydro-pyrido[1,2-a]indol-10-yl}acetic acid | 441 |

BIOLOGICAL ASSAYS

Radioligand Binding Assay.

Radioligand binding assays were performed at room temperature in 10 mM HEPES/KOH pH 7.4, 1 mM EDTA containing 10 mM $MnCl_2$ and 0.7 nM [$^3$H]$PGD_2$ (NEN, 171 Ci $mmol^{-1}$), in a final volume of 0.2 ml. Competing ligands were diluted in dimethylsulfoxide ($Me_2SO$) that was kept constant at 1% (v/v) of the final incubation volume. The reaction was initiated by the addition of 8-20 µg of membrane protein prepared from a HEK-hCRTH2 cell line. Total and non-specific binding were determined in the absence and the presence of 10 µM $PGD_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted Unifilters GF/C (Packard), using a Tomtec MachIII semi-automated harvester (for HEK-hCRTH2). The filters were then washed with 4 ml of the same buffer and residual radioligand bound to the filter was determined by liquid scintillation counting following equilibration in 25 µl Ultima Gold F™ (Unifilter) (Packard). The Ki (in nM) values for representative compounds of the present invention are as follows: ≤5: Examples 3.1, 5.1, 6.1, 7.1, 8.1/8A, 9.1, 26, 27.1, 28.1, 29.1, 30, 31.1, 31.3, 32.1, 32.4, 33.1, 34.1, 36.1, 38.1, 39, 40, 41; >5 and ≤10: Examples, 4, 5.3, 29.2; >10 and ≤50: Examples 1, 10, 14, 21, 22, 25, 31.4, 32.3, 35, 36.2, 37; >50 and ≤100: Examples 2, 5.4, 6.2, 27.2, 28.2; >100: Examples 3.2, 5.2, 7.2, 8.2, 9.2, 11, 12, 13, 15, 16, 17, 18, 19, 20, 23, 24, 31.2, 32.2, 33.2, 34.2, 38.2.

i[cAMP]Measurements.

HEK-hCRTH2 cells were grown to 80-90% confluency. On the day of the assay, the cells were washed with PBS, incubated for 2 min in cell dissociation buffer, harvested by centrifugation at 300 g for 5 min at room temperature and resuspended at 1.25e10$^6$ cells $ml^{-1}$ in Hanks' balanced salt solution containing 20 mM HEPES pH 7.4 and 0.75 mM IBMX (HBSS/HEPES/IBMX). The assay was performed in 384-plate format with 0.01 ml HBSS/HEPES/IBMX per well containing 12 500 cells and 75 nl of the test compound at various concentrations. Following a 10 min pre-incubation of the cells with the test compound at 37° C., 0.005 ml of Forskolin/DK-$PGD_2$ dilute in HBSS 20 mM Hepes, was added at a respectively final concentration of 10 uM and 150 nM, to initiate the reaction. After 10 min incubation at 37° C., the cAMP content was quantified using the cAMP XS+HitHunter chemiluminescence assay. (GE Healthcare 90-0075). % inhibition was calculated using the Forskolin and EC85 DK-PGD2 controls.

Eosinophil Shape Change Assay in Human Whole Blood.

Blood was collected in vacutainers containing EDTA. The antagonist was added to blood and incubated for 10 min at room temperature. DK-$PGD_2$ (13,14-dihydro-15-keto prostaglandin $D_2$) was then added to blood for 4 min at 37° C. in a running water bath. Blood cells were then fixed in presence of cold 0.25% (v/v) paraformaldehyde prepared in 75% (v/v) PBS for 1 min on ice. 1754 of fixed blood was transferred into 8704 of cold 155 mM $NH_4Cl$ lysis solution and incubated at 4° C. for at least 40 min. The solution was then centrifuged at 430 g for 5 min and the supernatant was discarded. Centrifuged cells were analyzed with a FACs Calibur flow cytometer (Becton Dickinson). Flow cytometry raw data were analyzed with FlowJo software by isolating the eosinophils from the neutrophils based on their high autofluorescence and determining the percent of total eosinophils with increased FSC-H value. Maximum (100%) and minimum (0%) shape change were determined in the presence of 10 µM DK-$PGD_2$ and PBS, respectively. A dose response curve with DK-$PGD_2$ was performed with every assay to determine the $EC_{50}$ for each blood donor. Compounds were tested in 10-dose titration curves in the presence of 30 nM DK-$PGD_2$ to determine an antagonist $IC_{50}$.

Some compounds of the present invention are selective for the CRTH2 receptor over the DP receptor. Assays on the DP, as well as other prostanoid, receptors are described in WO2003/06220.

What is claimed is:

1. A method of treating a prostaglandin mediated disease selected from the group consisting of nasal congestion and pulmonary congestion, comprising administering a therapeutically effective amount of a compound of formula (I)

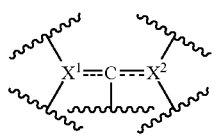

wherein:

$$X^1 = C = X^2$$

represents either

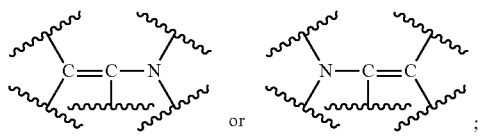 [SMILES: *C(*)=C(*)N(*)* ; *C(*)=C(*)N(*)*]

or ;

$Y_1$ is selected from optionally substituted aryl and —C($R_2$)($R_3$)($R_4$);
$Y_2$ is selected from H and —$C_{1-6}$alkyl;
Z is selected from H and —$C_{1-6}$alkyl;
$R_{1a}$ and $R_{1b}$ are independently selected from H, halogen, —O$C_{1-6}$alkyl, —O-halo$C_{1-6}$alkyl, —$C_{1-6}$alkyl, halo$C_{1-6}$alkyl, optionally substituted aryl and —($C_{1-3}$alkylene)-optionally substituted aryl;
$R_2$ is selected from H, —$C_{1-6}$alkyl optionally substituted with halogen, —OH or —NHSO$_2$CH$_3$, —OH, —O$C_{1-6}$alkyl, —S(O)$_n$$C_{1-6}$alkyl, —CN, optionally substituted aryl, optionally substituted —O-aryl and optionally substituted heteroaryl, wherein n is 0, 1 or 2;
$R_3$ is selected from H, —$C_{1-6}$alkyl, $C_{1-6}$haloalkyl, optionally substituted aryl and optionally substituted heteroaryl; and
$R_4$ is selected from H, —$C_{1-6}$alkyl, $C_{1-6}$haloalkyl, optionally substituted aryl and optionally substituted heteroaryl; or
$R_3$, $R_4$ and the carbon atom to which they are attached together form —$C_{3-6}$cycloalkyl, fluorenyl or —$C_{3-6}$heterocyclyl having a ring heteroatom selected from —N($R^a$)—, —O— and —S—; or
$R_3$, $R_4$ together represent $C_{1-6}$alkylidene;
$R^a$ is H, $C_{1-6}$alkyl or —C(O)$C_{1-6}$alkyl; and
the optional substituent for aryl and heteroaryl is 1 to 4 groups independently selected from halogen, —$C_{1-3}$alkoxy, —$C_{1-3}$haloalkyl, hydroxy-$C_{1-3}$alkyl, —S(O)n-$C_{1-3}$alkyl, amino, and mono- and di-($C_{1-3}$alkyl)amino;
or a pharmaceutically acceptable salt thereof to a mammalian patient in need thereof.

2. The method of claim 1, wherein the compound of the formula (I) has formula Ib

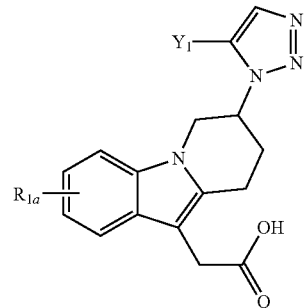

wherein $Y_1$ and $R_{1a}$ are as defined in claim 1.

3. The method of claim 2 wherein $Y_1$ is —C($R_3$)($R_4$)-optionally substituted phenyl or —CH$_2$O-optionally substituted phenyl; and
(i) one of $R_3$ and $R_4$ is H or OH, and the other is H, —$C_{1-3}$alkyl or optionally substituted phenyl; or (ii) $R_3$, $R_4$ and the carbon atom to which they are attached together form —$C_{3-6}$cycloalkyl; or (iii) $R_3$ and $R_4$ together represent —$C_{1-3}$alkylidene.

4. The method of claim 3 wherein $Y_1$ is —C($R_3$)($R_4$)-phenyl optionally substituted with 1 or 2 halogen atoms.

5. The method of claim 1, wherein the compound is {4-fluoro-7-[5-(4-fluorobenzyl)-1H-[1,2,3]triazol-1-yl]-6,7,8,9-tetrahydropyrido[1,2-a]indol-10-yl}-acetic acid.

6. The method of claim 1, wherein the compound is {(7R)-4-fluoro-7-[5-(4-fluorobenzyl)-1H-[1,2,3]triazol-1-yl]-6,7,8,9-tetrahydropyrido[1,2-a]indol-10-yl}-acetic acid or a pharmaceutically acceptable salt thereof.

7. The method of claim 1, wherein the prostaglandin-mediated disease is nasal congestion.

8. The method of claim 6, wherein the prostaglandin-mediated disease is nasal congestion.

9. The method of claim 7, wherein the mammalian patient is a human patient.

10. The method of claim 8, wherein the mammalian patient is a human patient.

* * * * *